US012076013B2

(12) United States Patent
Banerjee et al.

(10) Patent No.: US 12,076,013 B2
(45) Date of Patent: Sep. 3, 2024

(54) SURGICAL BUTTRESS ATTACHMENT ASSEMBLIES FOR SURGICAL STAPLING APPARATUS

(71) Applicant: Covidien LP, Mansfield, MA (US)

(72) Inventors: Saumya Banerjee, Collinsville, CT (US); Jacob C. Baril, Norwalk, CT (US)

(73) Assignee: Covidien LP, Mansfield, MA (US)

(*) Notice: Subject to any disclaimer, the term of this patent is extended or adjusted under 35 U.S.C. 154(b) by 384 days.

(21) Appl. No.: 17/392,670

(22) Filed: Aug. 3, 2021

(65) Prior Publication Data

US 2023/0040425 A1 Feb. 9, 2023

(51) Int. Cl.
*A61B 17/072* (2006.01)

(52) U.S. Cl.
CPC ...... *A61B 17/07292* (2013.01); *A61B 17/072* (2013.01); *A61B 2017/07264* (2013.01); *A61B 2017/07271* (2013.01)

(58) Field of Classification Search
CPC ............ A61B 17/072; A61B 17/07207; A61B 17/07271; A61B 17/07292; A61B 2017/07264; A61B 2017/07271
See application file for complete search history.

(56) References Cited

U.S. PATENT DOCUMENTS

| | | | |
|---|---|---|---|
| 3,054,406 | A | 9/1962 | Usher |
| 3,124,136 | A | 3/1964 | Usher |
| 3,364,200 | A | 1/1968 | Ashton et al. |
| 3,499,591 | A | 3/1970 | Green |
| 3,797,494 | A | 3/1974 | Zaffaroni |
| 3,939,068 | A | 2/1976 | Wendt et al. |
| 3,948,666 | A | 4/1976 | Kitanishi et al. |
| 4,064,062 | A | 12/1977 | Yurko |
| 4,166,800 | A | 9/1979 | Fong |
| 4,282,236 | A | 8/1981 | Broom |
| 4,347,847 | A | 9/1982 | Usher |
| 4,354,628 | A | 10/1982 | Green |
| 4,416,698 | A | 11/1983 | McCorsley, III |
| 4,429,695 | A | 2/1984 | Green |
| 4,452,245 | A | 6/1984 | Usher |
| 4,473,077 | A | 9/1984 | Noiles et al. |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

European Office Action corresponding to EP 14 17 2681.0 dated May 13, 2016.

(Continued)

*Primary Examiner* — Joshua G Kotis
(74) *Attorney, Agent, or Firm* — Carter, DeLuca & Farrell LLP

(57) ABSTRACT

Surgical buttress attachment assemblies for surgical stapling apparatus include a staple cartridge and a surgical buttress releasably secured to the staple cartridge. The staple cartridge includes buttress attachment features, such as posts, covers, and/or slots, and the surgical buttress are configured to engage the buttress attachment features of the staple cartridge.

14 Claims, 12 Drawing Sheets

201 270 272 278 276 277 258 268a 266 257 255 254 256 267 268 260 262 256b 270 272 278 276 266 267 266b 254 256 268 277 260

(56) References Cited

U.S. PATENT DOCUMENTS 4,605,730 A 8/1986 Shalaby et al.
4,626,253 A 12/1986 Broadnax, Jr.
4,655,221 A 4/1987 Devereux
4,834,090 A 5/1989 Moore
4,838,884 A 6/1989 Dumican et al.
4,927,640 A 5/1990 Dahlinder et al.
4,930,674 A 6/1990 Barak
5,002,551 A 3/1991 Linsky et al.
5,014,899 A 5/1991 Presty et al.
5,040,715 A 8/1991 Green et al.
5,057,334 A 10/1991 Vail
5,065,929 A 11/1991 Schulze et al.
5,112,496 A 5/1992 Dhawan et al.
5,162,430 A 11/1992 Rhee et al.
5,205,459 A 4/1993 Brinkerhoff et al.
5,263,629 A 11/1993 Trumbull et al.
5,281,197 A 1/1994 Arias et al.
5,307,976 A 5/1994 Olson et al.
5,312,023 A 5/1994 Green et al.
5,314,471 A 5/1994 Brauker et al.
5,318,221 A 6/1994 Green et al.
5,324,775 A 6/1994 Rhee et al.
5,326,013 A 7/1994 Green et al.
5,332,142 A 7/1994 Robinson et al.
5,344,454 A 9/1994 Clarke et al.
5,392,979 A 2/1995 Green et al.
5,397,324 A 3/1995 Carroll et al.
5,405,072 A 4/1995 Zlock et al.
5,410,016 A 4/1995 Hubbell et al.
5,425,745 A 6/1995 Green et al.
5,441,193 A 8/1995 Gravener
5,441,507 A 8/1995 Wilk
5,443,198 A 8/1995 Viola et al.
5,468,253 A 11/1995 Bezwada et al.
5,484,913 A 1/1996 Stilwell et al.
5,503,638 A 4/1996 Cooper et al.
5,514,379 A 5/1996 Weissleder et al.
5,542,594 A 8/1996 McKean et al.
5,543,441 A 8/1996 Rhee et al.
5,549,628 A 8/1996 Cooper et al.
5,550,187 A 8/1996 Rhee et al.
5,575,803 A 11/1996 Cooper et al.
5,645,915 A 7/1997 Kranzler et al.
5,653,756 A 8/1997 Clarke et al.
5,683,809 A 11/1997 Freeman et al.
5,690,675 A 11/1997 Sawyer et al.
5,702,409 A 12/1997 Rayburn et al.
5,752,965 A 5/1998 Francis et al.
5,752,974 A 5/1998 Rhee et al.
5,762,256 A 6/1998 Mastri et al.
5,766,188 A 6/1998 Igaki
5,769,892 A 6/1998 Kingwell
5,782,396 A 7/1998 Mastri et al.
5,799,857 A 9/1998 Robertson et al.
5,810,855 A 9/1998 Rayburn et al.
5,814,057 A 9/1998 Oi et al.
5,819,350 A 10/1998 Wang
5,833,695 A 11/1998 Yoon
5,843,096 A 12/1998 Igaki et al.
5,871,135 A 2/1999 Williamson IV et al.
5,874,500 A 2/1999 Rhee et al.
5,895,412 A 4/1999 Tucker
5,895,415 A 4/1999 Chow et al.
5,902,312 A 5/1999 Frater et al.
5,908,427 A 6/1999 McKean et al.
5,915,616 A 6/1999 Viola et al.
5,931,847 A 8/1999 Bittner et al.
5,957,363 A 9/1999 Heck
5,964,394 A 10/1999 Robertson
5,964,774 A 10/1999 McKean et al.
5,997,895 A 12/1999 Narotam et al.
6,019,791 A 2/2000 Wood
6,030,392 A 2/2000 Dakov
6,032,849 A 3/2000 Mastri et al.
6,045,560 A 4/2000 McKean et al.
6,063,097 A 5/2000 Oi et al.
6,080,169 A 6/2000 Turtel
6,093,557 A 7/2000 Pui et al.
6,099,551 A 8/2000 Gabbay
6,142,933 A 11/2000 Longo et al.
6,149,667 A 11/2000 Hovland et al.
6,152,943 A 11/2000 Sawhney
6,155,265 A 12/2000 Hammerslag
6,156,677 A 12/2000 Brown Reed et al.
6,165,201 A 12/2000 Sawhney et al.
6,179,862 B1 1/2001 Sawhney
6,210,439 B1 4/2001 Firmin et al.
6,214,020 B1 4/2001 Mulhauser et al.
6,241,139 B1 6/2001 Milliman et al.
6,258,107 B1 7/2001 Balazs et al.
6,267,772 B1 7/2001 Mulhauser et al.
6,270,530 B1 8/2001 Eldridge et al.
6,273,897 B1 8/2001 Dalessandro et al.
6,280,453 B1 8/2001 Kugel et al.
6,299,631 B1 10/2001 Shalaby
6,309,569 B1 10/2001 Farrar et al.
6,312,457 B1 11/2001 DiMatteo et al.
6,312,474 B1 11/2001 Francis et al.
6,325,810 B1 12/2001 Hamilton et al.
6,330,965 B1 12/2001 Milliman et al.
6,399,362 B1 6/2002 Pui et al.
6,436,030 B2 8/2002 Rehil
6,454,780 B1 9/2002 Wallace
6,461,368 B2 10/2002 Fogarty et al.
6,500,777 B1 12/2002 Wiseman et al.
6,503,257 B2 1/2003 Grant et al.
6,514,283 B2 2/2003 DiMatteo et al.
6,514,534 B1 2/2003 Sawhney
6,517,566 B1 2/2003 Hovland et al.
6,551,356 B2 4/2003 Rousseau
6,566,406 B1 5/2003 Pathak et al.
6,568,398 B2 5/2003 Cohen
6,590,095 B1 7/2003 Schleicher et al.
6,592,597 B2 7/2003 Grant et al.
6,605,294 B2 8/2003 Sawhney
6,610,006 B1 8/2003 Amid et al.
6,627,749 B1 9/2003 Kumar
6,638,285 B2 10/2003 Gabbay
6,652,594 B2 11/2003 Francis et al.
6,656,193 B2 12/2003 Grant et al.
6,656,200 B2 12/2003 Li et al.
6,669,735 B1 12/2003 Pelissier
6,673,093 B1 1/2004 Sawhney
6,677,258 B2 1/2004 Carroll et al.
6,685,714 B2 2/2004 Rousseau
6,702,828 B2 3/2004 Whayne
6,703,047 B2 3/2004 Sawhney et al.
6,704,210 B1 3/2004 Myers
6,723,114 B2 4/2004 Shalaby
6,726,706 B2 4/2004 Dominguez
6,736,823 B2 5/2004 Darois et al.
6,736,854 B2 5/2004 Vadurro et al.
6,746,458 B1 6/2004 Cloud
6,746,869 B2 6/2004 Pui et al.
6,764,720 B2 7/2004 Pui et al.
6,773,458 B1 8/2004 Brauker et al.
6,818,018 B1 11/2004 Sawhney
6,843,252 B2 1/2005 Harrison et al.
6,896,684 B2 5/2005 Monassevitch et al.
6,927,315 B1 8/2005 Heinecke et al.
6,939,358 B2 9/2005 Palacios et al.
6,946,196 B2 9/2005 Foss
6,953,139 B2 10/2005 Milliman et al.
6,959,851 B2 11/2005 Heinrich
7,009,034 B2 3/2006 Pathak et al.
7,025,772 B2 4/2006 Gellman et al.
7,060,087 B2 6/2006 DiMatteo et al.
7,087,065 B2 8/2006 Ulmsten et al.
7,108,701 B2 9/2006 Evens et al.
7,128,253 B2 10/2006 Mastri et al.
7,128,748 B2 10/2006 Mooradian et al.
7,134,438 B2 11/2006 Makower et al.
7,141,055 B2 11/2006 Abrams et al.
7,147,138 B2 12/2006 Shelton, IV

(56) References Cited

U.S. PATENT DOCUMENTS 7,160,299 B2 1/2007 Baily
7,179,268 B2 2/2007 Roy et al.
7,210,810 B1 5/2007 Iversen et al.
7,214,727 B2 5/2007 Kwon et al.
7,232,449 B2 6/2007 Sharkawy et al.
7,241,300 B2 7/2007 Sharkawy et al.
7,247,338 B2 7/2007 Pui et al.
7,279,322 B2 10/2007 Pui et al.
7,307,031 B2 12/2007 Carroll et al.
7,308,998 B2 12/2007 Mastri et al.
7,311,720 B2 12/2007 Mueller et al.
7,328,829 B2 2/2008 Arad et al.
7,334,717 B2 2/2008 Rethy et al.
7,347,850 B2 3/2008 Sawhney
7,377,928 B2 5/2008 Zubik et al.
7,434,717 B2 10/2008 Shelton, IV et al.
7,438,209 B1 10/2008 Hess et al.
7,464,849 B2 12/2008 Shelton, IV et al.
7,498,063 B2 3/2009 Pui et al.
7,547,312 B2 6/2009 Bauman et al.
7,559,937 B2 7/2009 de la Torre et al.
7,571,845 B2 8/2009 Viola
7,592,418 B2 9/2009 Pathak et al.
7,594,921 B2 9/2009 Browning
7,595,392 B2 9/2009 Kumar et al.
7,604,151 B2 10/2009 Hess et al.
7,611,494 B2 11/2009 Campbell et al.
7,635,073 B2 12/2009 Heinrich
7,645,874 B2 1/2010 Saferstein et al.
7,649,089 B2 1/2010 Kumar et al.
7,655,288 B2 2/2010 Bauman et al.
7,662,409 B2 2/2010 Masters
7,662,801 B2 2/2010 Kumar et al.
7,665,646 B2 2/2010 Prommersberger
7,666,198 B2 2/2010 Suyker et al.
7,669,747 B2 3/2010 Weisenburgh, II et al.
7,673,782 B2 3/2010 Hess et al.
7,708,180 B2 5/2010 Murray et al.
7,709,631 B2 5/2010 Harris et al.
7,717,313 B2 5/2010 Criscuolo et al.
7,722,642 B2 5/2010 Williamson, IV et al.
7,735,703 B2 6/2010 Morgan et al.
7,744,627 B2 6/2010 Orban, III et al.
7,754,002 B2 7/2010 Maase et al.
7,776,060 B2 8/2010 Mooradian et al.
7,789,889 B2 9/2010 Zubik et al.
7,793,813 B2 9/2010 Bettuchi
7,799,026 B2 9/2010 Schechter et al.
7,819,896 B2 10/2010 Racenet
7,823,592 B2 11/2010 Bettuchi et al.
7,824,420 B2 11/2010 Eldridge et al.
7,845,533 B2 12/2010 Marczyk et al.
7,845,536 B2 12/2010 Viola et al.
7,846,149 B2 12/2010 Jankowski
7,892,247 B2 2/2011 Conston et al.
7,909,224 B2 3/2011 Prommersberger
7,909,837 B2 3/2011 Crews et al.
7,938,307 B2 5/2011 Bettuchi
7,942,890 B2 5/2011 D'Agostino et al.
7,950,561 B2 * 5/2011 Aranyi ............ A61B 17/07292 227/176.1
7,951,166 B2 5/2011 Orban, III et al.
7,951,248 B1 5/2011 Fallis et al.
7,967,179 B2 6/2011 Olson et al.
7,988,027 B2 8/2011 Olson et al.
8,011,550 B2 9/2011 Aranyi et al.
8,011,555 B2 9/2011 Tarinelli et al.
8,016,177 B2 9/2011 Bettuchi et al.
8,016,178 B2 9/2011 Olson et al.
8,025,199 B2 9/2011 Whitman et al.
8,028,883 B2 10/2011 Stopek
8,033,483 B2 10/2011 Fortier et al.
8,033,983 B2 10/2011 Chu et al.
8,038,045 B2 10/2011 Bettuchi et al.
8,062,330 B2 11/2011 Prommersberger et al.
8,062,673 B2 11/2011 Figuly et al.
8,083,119 B2 12/2011 Prommersberger
8,091,756 B2 1/2012 Viola
8,123,766 B2 2/2012 Bauman et al.
8,123,767 B2 2/2012 Bauman et al.
8,127,975 B2 3/2012 Olson et al.
8,133,336 B2 3/2012 Kettlewell et al.
8,133,559 B2 3/2012 Lee et al.
8,146,791 B2 4/2012 Bettuchi et al.
8,152,777 B2 4/2012 Campbell et al.
8,157,149 B2 4/2012 Olson et al.
8,157,151 B2 4/2012 Ingmanson et al.
8,167,895 B2 5/2012 D'Agostino et al.
8,177,797 B2 5/2012 Shimoji et al.
8,178,746 B2 5/2012 Hildeberg et al.
8,192,460 B2 6/2012 Orban, III et al.
8,201,720 B2 6/2012 Hessler
8,210,414 B2 7/2012 Bettuchi et al.
8,210,453 B2 7/2012 Hull et al.
8,225,799 B2 7/2012 Bettuchi
8,225,981 B2 7/2012 Criscuolo et al.
8,231,043 B2 7/2012 Tarinelli et al.
8,235,273 B2 8/2012 Olson et al.
8,245,901 B2 8/2012 Stopek
8,252,339 B2 8/2012 Figuly et al.
8,252,921 B2 8/2012 Vignon et al.
8,256,654 B2 9/2012 Bettuchi et al.
8,257,391 B2 9/2012 Orban, III et al.
8,276,800 B2 10/2012 Bettuchi
8,286,849 B2 10/2012 Bettuchi
8,308,042 B2 * 11/2012 Aranyi ............ A61B 17/07292 227/176.1
8,308,045 B2 11/2012 Bettuchi et al.
8,308,046 B2 11/2012 Prommersberger
8,312,885 B2 11/2012 Bettuchi et al.
8,313,014 B2 11/2012 Bettuchi
8,317,790 B2 11/2012 Bell et al.
8,322,590 B2 12/2012 Patel et al.
8,348,126 B2 1/2013 Olson et al.
8,348,130 B2 1/2013 Shah et al.
8,365,972 B2 2/2013 Aranyi et al.
8,367,089 B2 2/2013 Wan et al.
8,371,491 B2 2/2013 Huitema et al.
8,371,492 B2 2/2013 Aranyi et al.
8,371,493 B2 2/2013 Aranyi et al.
8,372,094 B2 2/2013 Bettuchi et al.
8,393,514 B2 3/2013 Shelton, IV et al.
8,393,517 B2 3/2013 Milo
8,408,440 B2 4/2013 Olson et al.
8,408,480 B2 4/2013 Hull et al.
8,413,869 B2 4/2013 Heinrich
8,413,871 B2 4/2013 Racenet et al.
8,418,909 B2 4/2013 Kostrzewski
8,424,742 B2 4/2013 Bettuchi
8,453,652 B2 6/2013 Stopek
8,453,904 B2 6/2013 Eskaros et al.
8,453,909 B2 6/2013 Olson et al.
8,453,910 B2 6/2013 Bettuchi et al.
8,464,925 B2 6/2013 Hull et al.
8,470,360 B2 6/2013 McKay
8,474,677 B2 7/2013 Woodard, Jr. et al.
8,479,968 B2 7/2013 Hodgkinson et al.
8,485,414 B2 7/2013 Criscuolo et al.
8,496,683 B2 7/2013 Prommersberger et al.
8,511,533 B2 8/2013 Viola et al.
8,512,402 B2 8/2013 Marczyk et al.
8,518,440 B2 8/2013 Blaskovich et al.
8,529,600 B2 9/2013 Woodard, Jr. et al.
8,540,128 B2 9/2013 Shelton, IV et al.
8,540,131 B2 9/2013 Swayze
8,551,138 B2 10/2013 Orban, III et al.
8,556,918 B2 10/2013 Bauman et al.
8,561,873 B2 10/2013 Ingmanson et al.
8,579,990 B2 11/2013 Priewe
8,584,920 B2 11/2013 Hodgkinson
8,590,762 B2 11/2013 Hess et al.
8,616,430 B2 12/2013 (Prommersberger) Stopek et al.
8,617,132 B2 12/2013 Golzarian et al.
8,631,989 B2 1/2014 Aranyi et al.

(56) References Cited

U.S. PATENT DOCUMENTS 8,646,674 B2 2/2014 Schulte et al.
8,668,129 B2 3/2014 Olson
8,678,263 B2 3/2014 Viola
8,679,137 B2 3/2014 Bauman et al.
8,684,250 B2 4/2014 Bettuchi et al.
8,701,958 B2 4/2014 Shelton, IV et al.
8,721,703 B2 5/2014 Fowler
8,727,197 B2 5/2014 Hess et al.
8,757,466 B2 6/2014 Olson et al.
8,789,737 B2 7/2014 Hodgkinson et al.
8,814,888 B2 8/2014 Sgro
8,820,606 B2 9/2014 Hodgkinson
8,827,133 B2 9/2014 Shelton, IV et al.
8,828,023 B2 9/2014 Neff et al.
8,857,694 B2 10/2014 Shelton, IV et al.
8,864,009 B2 10/2014 Shelton, IV et al.
8,870,050 B2 10/2014 Hodgkinson
8,920,443 B2 12/2014 Hiles et al.
8,920,444 B2 12/2014 Hiles et al.
8,939,344 B2 1/2015 Olson et al.
8,956,390 B2 2/2015 Shah et al.
8,967,448 B2 3/2015 Carter et al.
9,005,243 B2 4/2015 Stopek et al.
9,010,606 B2 4/2015 Aranyi et al.
9,010,608 B2 4/2015 Casasanta, Jr. et al.
9,010,609 B2 4/2015 Carter et al.
9,010,610 B2 4/2015 Hodgkinson
9,010,612 B2 4/2015 Stevenson et al.
9,016,543 B2 4/2015 (Prommersberger) Stopek et al.
9,016,544 B2 4/2015 Hodgkinson et al.
9,027,817 B2 5/2015 Milliman et al.
9,044,227 B2 6/2015 Shelton, IV et al.
9,055,944 B2 6/2015 Hodgkinson et al.
9,084,602 B2 7/2015 Gleiman
9,107,665 B2 8/2015 Hodgkinson et al.
9,107,667 B2 8/2015 Hodgkinson
9,113,871 B2 8/2015 Milliman et al.
9,113,873 B2 8/2015 Marczyk et al.
9,113,885 B2 8/2015 Hodgkinson et al.
9,113,893 B2 8/2015 Sorrentino et al.
9,161,753 B2 10/2015 Prior
9,161,757 B2 10/2015 Bettuchi
9,186,140 B2 11/2015 Hiles et al.
9,186,144 B2 11/2015 Stevenson et al.
9,192,378 B2 11/2015 Aranyi et al.
9,192,379 B2 11/2015 Aranyi et al.
9,192,380 B2 11/2015 (Tarinelli) Racenet et al.
9,192,383 B2 11/2015 Milliman
9,192,384 B2 11/2015 Bettuchi
9,198,660 B2 12/2015 Hodgkinson
9,198,663 B1 12/2015 Marczyk et al.
9,204,881 B2 12/2015 Penna
9,220,504 B2 12/2015 Viola et al.
9,226,754 B2 1/2016 D'Agostino et al.
9,237,892 B2 1/2016 Hodgkinson
9,237,893 B2 1/2016 Carter et al.
9,277,922 B2 3/2016 Carter et al.
9,295,466 B2 3/2016 Hodgkinson et al.
9,326,768 B2 5/2016 Shelton, IV
9,326,773 B2 5/2016 Casasanta, Jr. et al.
9,328,111 B2 5/2016 Zhou et al.
9,345,479 B2 5/2016 (Tarinelli) Racenet et al.
9,351,729 B2 5/2016 Orban, III et al.
9,351,731 B2 5/2016 Carter et al.
9,351,732 B2 5/2016 Hodgkinson
9,358,005 B2 6/2016 Shelton, IV et al.
9,364,229 B2 6/2016 D'Agostino et al.
9,364,234 B2 6/2016 (Prommersberger) Stopek et al.
9,386,988 B2 7/2016 Baxter, III et al.
9,402,627 B2 8/2016 Stevenson et al.
9,414,839 B2 8/2016 Penna
9,433,412 B2 9/2016 Bettuchi et al.
9,433,413 B2 9/2016 Stopek
9,433,420 B2 * 9/2016 Hodgkinson .... A61B 17/07207
9,445,812 B2 9/2016 Olson et al.
9,445,817 B2 9/2016 Bettuchi
9,463,260 B2 10/2016 Stopek
9,486,215 B2 11/2016 Olson et al.
9,492,170 B2 11/2016 Bear et al.
9,504,470 B2 11/2016 Milliman
9,517,164 B2 12/2016 Vitaris et al.
9,572,576 B2 2/2017 Hodgkinson et al.
9,585,657 B2 3/2017 Shelton, IV et al.
9,597,077 B2 3/2017 Hodgkinson
9,610,080 B2 4/2017 Whitfield et al.
9,622,745 B2 4/2017 Ingmanson et al.
9,629,626 B2 4/2017 Soltz et al.
9,636,850 B2 5/2017 Stopek (nee Prommersberger) et al.
9,655,620 B2 5/2017 Prescott et al.
9,675,351 B2 * 6/2017 Hodgkinson ...... A61B 17/1155
9,681,936 B2 6/2017 Hodgkinson et al.
9,687,262 B2 6/2017 Rousseau et al.
9,693,772 B2 7/2017 Ingmanson et al.
9,708,184 B2 7/2017 Chan et al.
9,770,245 B2 9/2017 Swayze et al.
9,775,617 B2 10/2017 Carter et al.
9,775,618 B2 10/2017 Bettuchi et al.
9,782,173 B2 10/2017 Mozdzierz
9,844,378 B2 12/2017 Casasanta et al.
9,918,713 B2 3/2018 Zergiebel et al.
9,931,116 B2 4/2018 Racenet et al.
10,022,125 B2 7/2018 (Prommersberger) Stopek
10,098,639 B2 10/2018 Hodgkinson
10,111,659 B2 10/2018 Racenet et al.
10,154,840 B2 12/2018 Viola et al.
10,426,468 B2 10/2019 Contini et al.
10,646,221 B2 * 5/2020 Shelton, IV ..... A61B 17/07207
10,716,564 B2 * 7/2020 Shelton, IV ..... A61B 17/07292
10,952,729 B2 * 3/2021 Williams ......... A61B 17/07292
11,026,686 B2 * 6/2021 Aranyi ............. A61B 17/07292
11,751,875 B2 * 9/2023 Baril ................ A61B 17/07207 227/176.1
2002/0091397 A1 7/2002 Chen
2002/0151911 A1 10/2002 Gabbay
2003/0065345 A1 4/2003 Weadock
2003/0078209 A1 4/2003 Schmidt
2003/0083676 A1 5/2003 Wallace
2003/0125676 A1 7/2003 Swenson et al.
2003/0181927 A1 9/2003 Wallace
2003/0208231 A1 11/2003 Williamson et al.
2004/0092912 A1 5/2004 Jinno et al.
2004/0107006 A1 6/2004 Francis et al.
2004/0131418 A1 7/2004 Budde et al.
2004/0254590 A1 12/2004 Hoffman et al.
2004/0260315 A1 12/2004 Dell et al.
2005/0002981 A1 1/2005 Lahtinen et al.
2005/0006429 A1 1/2005 Wales et al.
2005/0021085 A1 1/2005 Abrams et al.
2005/0059996 A1 3/2005 Bauman et al.
2005/0059997 A1 3/2005 Bauman et al.
2005/0070929 A1 3/2005 Dalessandro et al.
2005/0118435 A1 6/2005 DeLucia et al.
2005/0149073 A1 7/2005 Arani et al.
2005/0283256 A1 12/2005 Sommerich et al.
2006/0008505 A1 1/2006 Brandon
2006/0025816 A1 2/2006 Shelton, IV
2006/0121266 A1 6/2006 Fandel et al.
2006/0173470 A1 8/2006 Oray et al.
2006/0190027 A1 8/2006 Downey
2007/0034669 A1 2/2007 de la Torre et al.
2007/0203510 A1 8/2007 Bettuchi
2007/0243227 A1 10/2007 Gertner
2007/0246505 A1 10/2007 Pace-Floridia et al.
2008/0009811 A1 1/2008 Cantor
2008/0029570 A1 2/2008 Shelton et al.
2008/0082126 A1 4/2008 Murray et al.
2008/0140115 A1 6/2008 Stopek
2008/0169328 A1 7/2008 Shelton
2008/0169332 A1 7/2008 Shelton et al.
2008/0169333 A1 7/2008 Shelton et al.
2008/0216855 A1 9/2008 Nasca
2008/0220047 A1 9/2008 Sawhney et al.
2008/0290134 A1 11/2008 Bettuchi et al.

(56) References Cited

U.S. PATENT DOCUMENTS

| | | | |
|---|---|---|---|
| 2009/0001121 | A1 | 1/2009 | Hess et al. |
| 2009/0001130 | A1 | 1/2009 | Hess et al. |
| 2009/0031842 | A1 | 2/2009 | Kawai et al. |
| 2009/0206125 | A1 | 8/2009 | Huitema et al. |
| 2009/0206126 | A1 | 8/2009 | Huitema et al. |
| 2009/0206139 | A1 | 8/2009 | Hall et al. |
| 2009/0206141 | A1 | 8/2009 | Huitema et al. |
| 2009/0206142 | A1 | 8/2009 | Huitema et al. |
| 2009/0218384 | A1* | 9/2009 | Aranyi ............ A61B 17/07207 227/176.1 |
| 2009/0277944 | A9 | 11/2009 | Dalessandro et al. |
| 2010/0016855 | A1 | 1/2010 | Ramstein et al. |
| 2010/0016888 | A1 | 1/2010 | Calabrese et al. |
| 2010/0087840 | A1 | 4/2010 | Ebersole et al. |
| 2010/0147921 | A1 | 6/2010 | Olson |
| 2010/0147922 | A1 | 6/2010 | Olson |
| 2010/0174253 | A1 | 7/2010 | Cline et al. |
| 2010/0203151 | A1 | 8/2010 | Hiraoka |
| 2010/0243707 | A1 | 9/2010 | Olson et al. |
| 2010/0331859 | A1 | 12/2010 | Omori |
| 2011/0034910 | A1 | 2/2011 | Ross et al. |
| 2011/0089220 | A1 | 4/2011 | Ingmanson et al. |
| 2011/0125138 | A1 | 5/2011 | Malinouskas et al. |
| 2011/0166673 | A1 | 7/2011 | Patel et al. |
| 2011/0215133 | A1 | 9/2011 | Aranyi |
| 2011/0293690 | A1 | 12/2011 | Griffin et al. |
| 2012/0080336 | A1 | 4/2012 | Shelton, IV et al. |
| 2012/0197272 | A1 | 8/2012 | Oray et al. |
| 2012/0241491 | A1 | 9/2012 | Aldridge et al. |
| 2012/0241493 | A1 | 9/2012 | Baxter, III et al. |
| 2012/0253298 | A1 | 10/2012 | Henderson et al. |
| 2013/0075446 | A1 | 3/2013 | Wang et al. |
| 2013/0153636 | A1 | 6/2013 | Shelton, IV et al. |
| 2013/0153641 | A1 | 6/2013 | Shelton, IV et al. |
| 2013/0256380 | A1 | 10/2013 | Schmid et al. |
| 2014/0048580 | A1 | 2/2014 | Merchant et al. |
| 2014/0131418 | A1 | 5/2014 | Kostrzewski |
| 2014/0224686 | A1 | 8/2014 | Aronhalt et al. |
| 2014/0239047 | A1 | 8/2014 | Hodgkinson et al. |
| 2015/0041347 | A1 | 2/2015 | Hodgkinson |
| 2015/0133995 | A1 | 5/2015 | Shelton, IV et al. |
| 2015/0157321 | A1 | 6/2015 | Zergiebel et al. |
| 2015/0209045 | A1 | 7/2015 | Hodgkinson et al. |
| 2015/0231409 | A1 | 8/2015 | Racenet et al. |
| 2015/0327864 | A1 | 11/2015 | Hodgkinson et al. |
| 2016/0022268 | A1 | 1/2016 | Prior |
| 2016/0045200 | A1 | 2/2016 | Milliman |
| 2016/0100834 | A1 | 4/2016 | Viola et al. |
| 2016/0106430 | A1 | 4/2016 | Carter et al. |
| 2016/0128694 | A1 | 5/2016 | Baxter, III et al. |
| 2016/0157857 | A1 | 6/2016 | Hodgkinson et al. |
| 2016/0174988 | A1 | 6/2016 | D'Agostino et al. |
| 2016/0206315 | A1 | 7/2016 | Olson |
| 2016/0220257 | A1 | 8/2016 | Casasanta et al. |
| 2016/0249923 | A1 | 9/2016 | Hodgkinson et al. |
| 2016/0270793 | A1 | 9/2016 | Carter et al. |
| 2016/0310143 | A1 | 10/2016 | Bettuchi |
| 2016/0338704 | A1 | 11/2016 | Penna |
| 2016/0367252 | A1 | 12/2016 | Olson et al. |
| 2016/0367253 | A1 | 12/2016 | Hodgkinson |
| 2016/0367257 | A1 | 12/2016 | Stevenson et al. |
| 2017/0042540 | A1 | 2/2017 | Olson et al. |
| 2017/0049452 | A1 | 2/2017 | Milliman |
| 2017/0119390 | A1 | 5/2017 | Schellin et al. |
| 2017/0150967 | A1 | 6/2017 | Hodgkinson et al. |
| 2017/0172575 | A1 | 6/2017 | Hodgkinson |
| 2017/0231629 | A1 | 8/2017 | Stopek et al. |
| 2017/0238931 | A1 | 8/2017 | Prescott et al. |
| 2017/0281328 | A1 | 10/2017 | Hodgkinson, Ph.D et al. |
| 2017/0296188 | A1 | 10/2017 | Ingmanson et al. |
| 2017/0354415 | A1 | 12/2017 | Casasanta, Jr. et al. |
| 2018/0125491 | A1 | 5/2018 | Aranyi |
| 2018/0140301 | A1 | 5/2018 | Milliman |
| 2018/0168654 | A1 | 6/2018 | Hodgkinson et al. |
| 2018/0214147 | A1 | 8/2018 | Merchant et al. |
| 2018/0229054 | A1 | 8/2018 | Racenet et al. |
| 2018/0250000 | A1 | 9/2018 | Hodgkinson et al. |
| 2018/0256164 | A1 | 9/2018 | Aranyi |
| 2018/0296214 | A1 | 10/2018 | Hodgkinson et al. |
| 2018/0310937 | A1 | 11/2018 | (Prommersberger) Stopek et al. |
| 2019/0021734 | A1 | 1/2019 | Hodgkinson |
| 2019/0059878 | A1 | 2/2019 | (Tarinelli) Racenet et al. |
| 2019/0083087 | A1 | 3/2019 | Viola et al. |
| 2019/0328390 | A1 | 10/2019 | Harris et al. |
| 2020/0107830 | A1* | 4/2020 | Williams ......... A61B 17/07292 |
| 2021/0106329 | A1* | 4/2021 | Williams ............... A61B 17/11 |

FOREIGN PATENT DOCUMENTS

| | | | |
|---|---|---|---|
| DE | 19924311 | A1 | 11/2000 |
| EP | 0327022 | A2 | 8/1989 |
| EP | 0594148 | A1 | 4/1994 |
| EP | 2491867 | A1 | 8/2012 |
| JP | 2000166933 | A | 6/2000 |
| JP | 2002202213 | A | 7/2002 |
| JP | 2007124166 | A | 5/2007 |
| JP | 2010214132 | A | 9/2010 |
| WO | 9005489 | A1 | 5/1990 |
| WO | 95/16221 | A1 | 6/1995 |
| WO | 98/38923 | A1 | 9/1998 |
| WO | 9926826 | A2 | 6/1999 |
| WO | 0010456 | A1 | 3/2000 |
| WO | 0016684 | A1 | 3/2000 |
| WO | 2010075298 | A2 | 7/2010 |

OTHER PUBLICATIONS

Extended European Search Report corresponding to EP 16 15 3647.9 dated Jun. 3, 2016.

Chinese Office Action corresponding to CN 201210545228 dated Jun. 29, 2016.

Japanese Office Action corresponding to JP 2012-250058 mailed Jun. 29, 2016.

European Office Action corresponding to EP 14 15 7997.9 dated Jun. 29, 2016.

Canadian Office Action corresponding to CA 2,712,617 dated Jun. 30, 2016.

Chinese First Office Action corresponding to CN 2013103036903 dated Jun. 30, 2016.

Australian Patent Examination Report No. 1 corresponding to AU 2012250278 dated Jul. 10, 2016.

Australian Patent Examination Report No. 1 corresponding to AU 2012244382 dated Jul. 10, 2016.

Japanese Office Action corresponding to 2012-255242 mailed Jul. 26, 2016.

Japanese Office Action corresponding to JP 2012-268668 mailed Jul. 27, 2016.

European Office Action corresponding to EP 14 15 2060.1 dated Aug. 4, 2016.

European Office Action corresponding to EP 12 16 5609.4 dated Aug. 5, 2016.

European Office Action corresponding to EP 15 15 2392.5 dated Aug. 8, 2016.

Japanese Office Action corresponding to JP 2013-003624 mailed Aug. 25, 2016.

Australian Patent Examination Report No. 1 corresponding to AU 2012261752 dated Sep. 6, 2016.

Japanese Office Action corresponding to JP 2014-252703 mailed Sep. 26, 2016.

European Office Action corresponding to EP 12 19 8776.2 dated Sep. 12, 2016.

Japanese Office Action corresponding to JP 2013-000321 mailed Sep. 13, 2016.

Chinese Second Office Action corresponding to CN 201310353628.5 dated Sep. 26, 2016.

European Office Action corresponding to EP 12 15 2541.4 dated Sep. 27, 2016.

Australian Patent Examination Report No. 1 corresponding to AU 2012268923 dated Sep. 28, 2016.

(56) References Cited

OTHER PUBLICATIONS

Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 mailed May 23, 2017.
European Office Action corresponding to EP 12 19 4784.0 dated May 29, 2017.
Japanese Office Action corresponding to JP 2013-169083 mailed May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 mailed Aug. 17, 2017.
Japanese Office Action corresponding to JP 2013-229471 mailed Aug. 17, 2017.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 mailed Sep. 11, 2015.
Canadian First Office Action corresponding to CA 2,686, 105 dated Sep. 17, 2015.
Japanese Office Action corresponding to JP 2012-040188 mailed Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 mailed Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.

(56) References Cited

OTHER PUBLICATIONS

European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 mailed May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
International Search Report and Written Opinion issued in corresponding International Application No. PCT/IB2022/056946 dated Oct. 19, 2022, 17 pages.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 mailed Oct. 20, 2017.
Japanese Office Action corresponding to JP 2013-147701 mailed Oct. 27, 2017.
Extended European Search Report corresponding to EP 17 17 5656.2 dated Nov. 7, 2017.
Japanese Office Action corresponding to JP 2014-009738 mailed Nov. 14, 2017.
European Office Action corresponding to EP 13 17 3986.4 dated Nov. 29, 2017.
Japanese Office Action corresponding to JP 2017-075975 mailed Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 mailed Jan. 15, 2018.
Australian Examination Report No. 1 corresponding to Patent Application AU 2017225037 dated Jan. 23, 2018.
Japanese Office Action corresponding to Patent Application JP 2013-229471 mailed May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
European Search Report corresponding to EP 06 00 4598, completed Jun. 22, 2006; (2 pp).
European Search Report corresponding to EP 06 01 6962.0, completed Jan. 3, 2007 and mailed Jan. 11, 2007; (10 pp).
International Search Report corresponding to International Application No. PCT/US2005/036740, completed Feb. 20, 2007 and mailed Mar. 23, 2007; (8 pp).
International Search Report corresponding to International Application No. PCT/US2007/022713, completed Apr. 21, 2008 and mailed May 15, 2008; (1 p).
International Search Report corresponding to International Application No. PCT/US2008/002981, completed Jun. 9, 2008 and mailed Jun. 26, 2008; (2 pp).
European Search Report corresponding to EP 08 25 1779, completed Jul. 14, 2008 and mailed Jul. 23, 2008; (5 pp).
European Search Report corresponding to EP 08 25 1989.3, completed Mar. 11, 2010 and mailed Mar. 24, 2010; (6 pp).
European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).
European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 2013; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).

(56) References Cited

OTHER PUBLICATIONS

Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 13 19 2111.6, completed Feb. 13, 2014 and mailed Feb. 27, 2014; (10 pp).
Extended European Search Report corresponding to EP 13 19 5919.9, completed Feb. 10, 2014 and mailed Mar. 3, 2014; (7 pp).
Extended European Search Report corresponding to EP 08 72 6500.5, completed Feb. 20, 2014 and mailed Mar. 3, 2014; (7 pp).
Extended European Search Report corresponding to EP 13 19 5019.8, completed Mar. 14, 2014 and mailed Mar. 24, 2014; (7 pp).
Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 13 19 4995.0, completed Jun. 5, 2014 and mailed Jun. 16, 2014; (5 pp).
Extended European Search Report corresponding to EP 14 15 7195.0, completed Jun. 5, 2014 and mailed Jun. 18, 2014; (9 pp).
Extended European Search Report corresponding to EP 14 15 6342.9, completed Jul. 22, 2014 and mailed Jul. 29, 2014; (8 pp).

* cited by examiner 134
134a
134b
140
144
146
142
152
101
154a
164
4
175
170a
174
178
157
155
158
156
154
172
162
160a
160
170
178
176
166
160b
5
170b
177

164
175
175
164
174
170a
172
170
154
177
170b
176
166

SURGICAL BUTTRESS ATTACHMENT ASSEMBLIES FOR SURGICAL STAPLING APPARATUS

FIELD

This disclosure is generally related to surgical stapling apparatus, and more particularly, to surgical buttress attachment assemblies for releasably securing surgical buttresses to the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or “fired”, longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon. The buttress material reinforces the staple or suture line as well as covers the juncture of the body tissues to reduce leakage prior to healing.

SUMMARY

This disclosure relates to surgical buttress attachment onto a surgical stapling apparatus. Surgical buttress attachment assemblies of this disclosure are designed to make surgical buttress attachment a simple, straightforward, and cost-effective procedure.

The surgical buttress attachment assemblies of this disclosure may include a surgical buttress having attachment features fabricated to the tolerance of a staple cartridge on which the surgical buttress is releasably secured to provide, for example, ease in loading the surgical buttress onto the staple cartridge (e.g., by the manufacture or by a user) and/or ease of clinical preparation and use. The surgical buttress attachment assemblies may include a staple cartridge having molded attachment features that may provide cost savings and/or ease in manufacture as compared to surgical buttress attachment features and methods requiring additional materials and/or processing steps.

The surgical buttress attachment assemblies may enable manufacturer and/or user side assembly with a reduced number of assembly steps as compared to conventional methods of loading a surgical buttress onto a staple cartridge which, in turn, may reduce assembly costs and/or assembly inconsistencies or errors. Further, the surgical buttress attachment assemblies may also minimize or prevent the surgical buttress from being elongated and/or deformed during assembly, enabling the staple lines to remain flush with the surgical buttress so that staple formation is not adversely affected during use. Further still, the surgical buttress attachment assemblies enable fixation of the surgical buttress on the staple cartridge during use of the surgical stapling apparatus. Movement of the surgical buttress relative to the staple cartridge is minimized or prevented until the surgical stapling apparatus is fired (e.g., during prewetting processes, introduction into tissue (e.g., via a trocar), manipulation within tissue, etc.).

In aspects, this disclosure provides a surgical buttress attachment assembly including a staple cartridge and a surgical buttress. The staple cartridge includes a cartridge body and a cartridge tip extending distally from the cartridge body. The cartridge body has a tissue facing surface including staple pockets defined therein and the cartridge tip includes an inner surface extending distally from the tissue facing surface. The cartridge body includes proximal posts extending outwardly from the tissue facing surface and the cartridge tip includes a distal post extending outwardly from the inner surface. The surgical buttress includes a body, a proximal tab extending proximally from the body, and a distal tab extending distally from the body. The proximal tab is engaged with the proximal posts of the cartridge body and the distal tab is engaged with the distal post of the cartridge tip to retain the surgical buttress on the staple cartridge.

In some aspects, the proximal posts of the cartridge body are proximal to the staple pockets. In some aspects, the tissue facing surface of the cartridge body includes a central longitudinal slot defined therein, and the proximal posts are disposed on opposed sides of the central longitudinal slot. In certain aspects, the distal post of the cartridge tip is axially aligned with the central longitudinal slot of the cartridge body. In some aspects, the distal post includes an elongate body extending from the inner surface of the cartridge tip and a flange extending distally from the elongate body.

In some aspects, the proximal and distal tabs of the surgical buttress respectively define proximal and distal openings, and the proximal and distal posts extend through the proximal and distal openings. In some aspects, the body of the surgical buttress is delineated from the proximal and distal tabs by perforations extending transversely through the surgical buttress.

The staple cartridge may further include a tip cover pivotably coupled to the cartridge tip, and the distal tab of the surgical buttress may be retained between the cartridge tip and the tip cover. In some aspects, a distal end of the tip cover is coupled to a distal end of the cartridge tip by a hinge. In some aspects, the tip cover is movable between an open position, in which the inner surface of the cartridge tip is uncovered, and a closed position, in which the inner surface of the cartridge tip is covered. In certain aspects, the tip cover defines an aperture therethrough, and the distal post of the cartridge tip extends through the aperture when the tip cover is in the closed position.

In aspects, this disclosure provides a surgical buttress attachment assembly including a staple cartridge and a surgical buttress. The staple cartridge includes a cartridge body, a cartridge tip extending distally from the cartridge body, and a tip cover pivotably coupled to the cartridge tip. The cartridge body has a tissue facing surface including staple pockets defined therein and the cartridge tip includes an inner surface extending distally from the tissue facing surface. The cartridge body includes proximal posts extending outwardly from the tissue facing surface. The surgical buttress includes a body, a proximal tab extending proximally from the body, and a distal tab extending distally from the body. The proximal tab is engaged with the proximal posts and the distal tab is engaged between the cartridge tip and the tip cover to retain the surgical buttress on the staple cartridge.

In some aspects, a distal end of the tip cover is coupled to a distal end of the cartridge tip by a hinge. In some aspects, the tip cover is movable between an open position, in which the inner surface of the cartridge tip is uncovered, and a closed position, in which the inner surface of the cartridge tip is covered.

The cartridge tip may include a distal post extending outwardly from the inner surface. In some aspects, the tip cover defines an aperture therethrough, and the distal post of the cartridge tip extends through the aperture when the tip cover is in the closed position. In certain aspects, the distal post includes an elongate body extending from the inner surface of the cartridge tip and a flange extending distally from the elongate body, and the tip cover engages the flange of the distal post when the tip cover is in the closed position.

In aspects, this disclosure provides a surgical buttress attachment assembly including a staple cartridge and a surgical buttress. The staple cartridge has a tissue facing surface including staple pockets and longitudinal slots defined therein. The surgical buttress includes a body and longitudinal tabs extending from the body. The longitudinal tabs are releasably retained within the longitudinal slots of the staple cartridge.

In some aspects, the longitudinal slots are disposed laterally outwardly of the staple pockets on opposed sides of the staple cartridge. In some aspects, the longitudinal slots extend proximally and distally beyond the staple pockets.

The details of one or more aspects of this disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of this disclosure are described hereinbelow with reference to the drawings, which are incorporated in and constitute a part of this specification, wherein.

DETAILED DESCRIPTION

Figure 1:
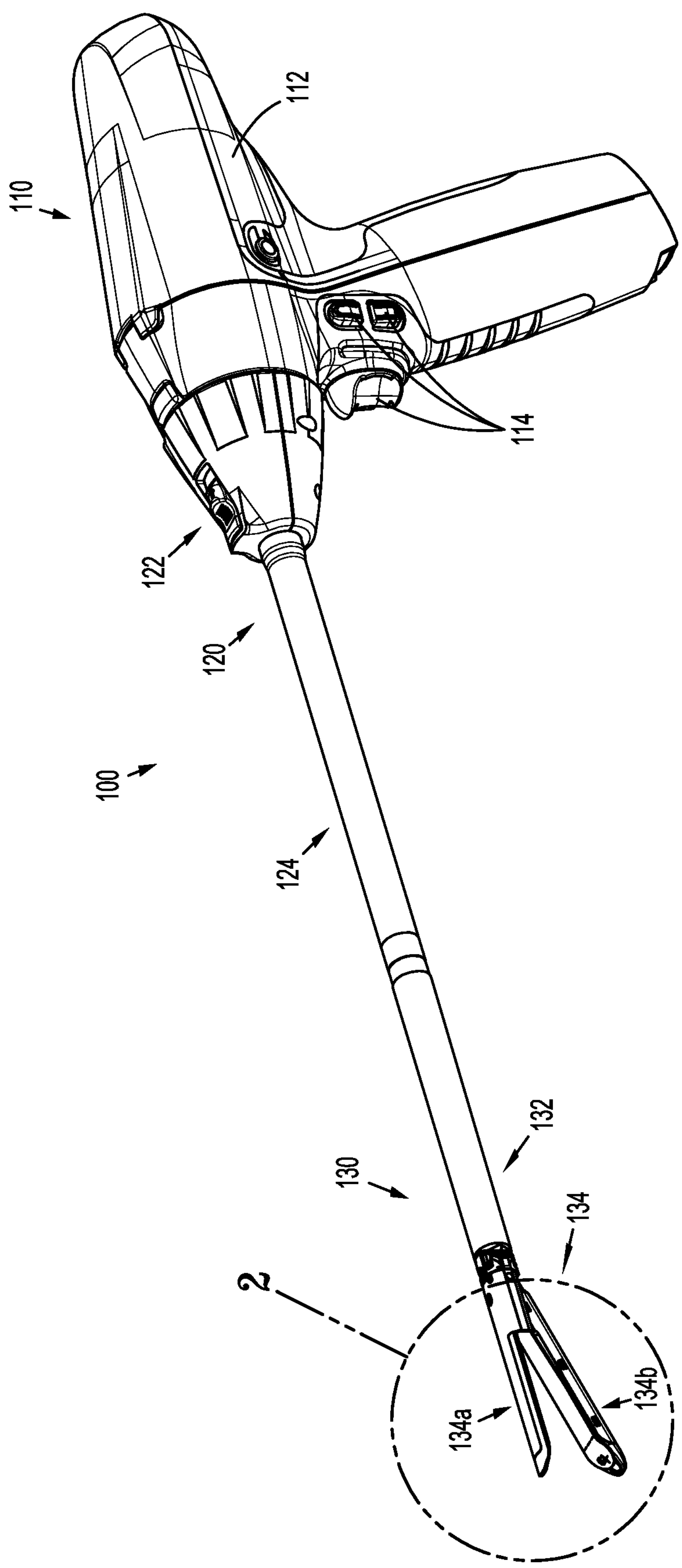
FIG. 1 is a perspective view of a surgical stapling apparatus in accordance with aspects of the disclosure.

Aspects of this disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Further, it should be understood that various elements of the disclosure, such as those numbered in the 100 series, correspond to elements of the disclosure similarly numbered in the 200 and 300 series, such that redundant explanation of similar elements need not be repeated herein.

Turning now to FIG. 1, an exemplary surgical device or surgical stapling apparatus 100 is shown in accordance with aspects of the disclosure. The surgical stapling apparatus 100 generally includes a handle assembly 110, an adapter assembly 120, and a loading unit 130. The handle assembly 110 is configured for selective connection with the adapter assembly 120 and, in turn, the adapter assembly 120 is configured for selective connection with the loading unit 130.

The surgical stapling apparatus 100 will further be described to the extent necessary to disclose aspects of the disclosure. For a detailed description of the structure and function of an exemplary surgical stapling apparatus 100, reference may be made to U.S. Pat. No. 10,426,468, the entire content of which is incorporated herein by reference.

The handle assembly 110 includes a handle housing 112 housing a power-pack (not shown) configured to power and control various operations of the surgical stapling apparatus 100, and a plurality of actuators 114 (e.g., finger-actuated control buttons, knobs, toggles, slides, interfaces, and the like) for activating various functions of the surgical stapling apparatus 100. The adapter assembly 120 includes a knob housing 122 configured for operable connection to the handle assembly 110 and an elongate tubular body 124 configured for operable connection to the loading unit 130. Alternatively, the elongate tubular body 124 may be supported directly on the handle assembly 110 (e.g., permanently affixed to or integrally formed with the handle assembly).

Figure 3:
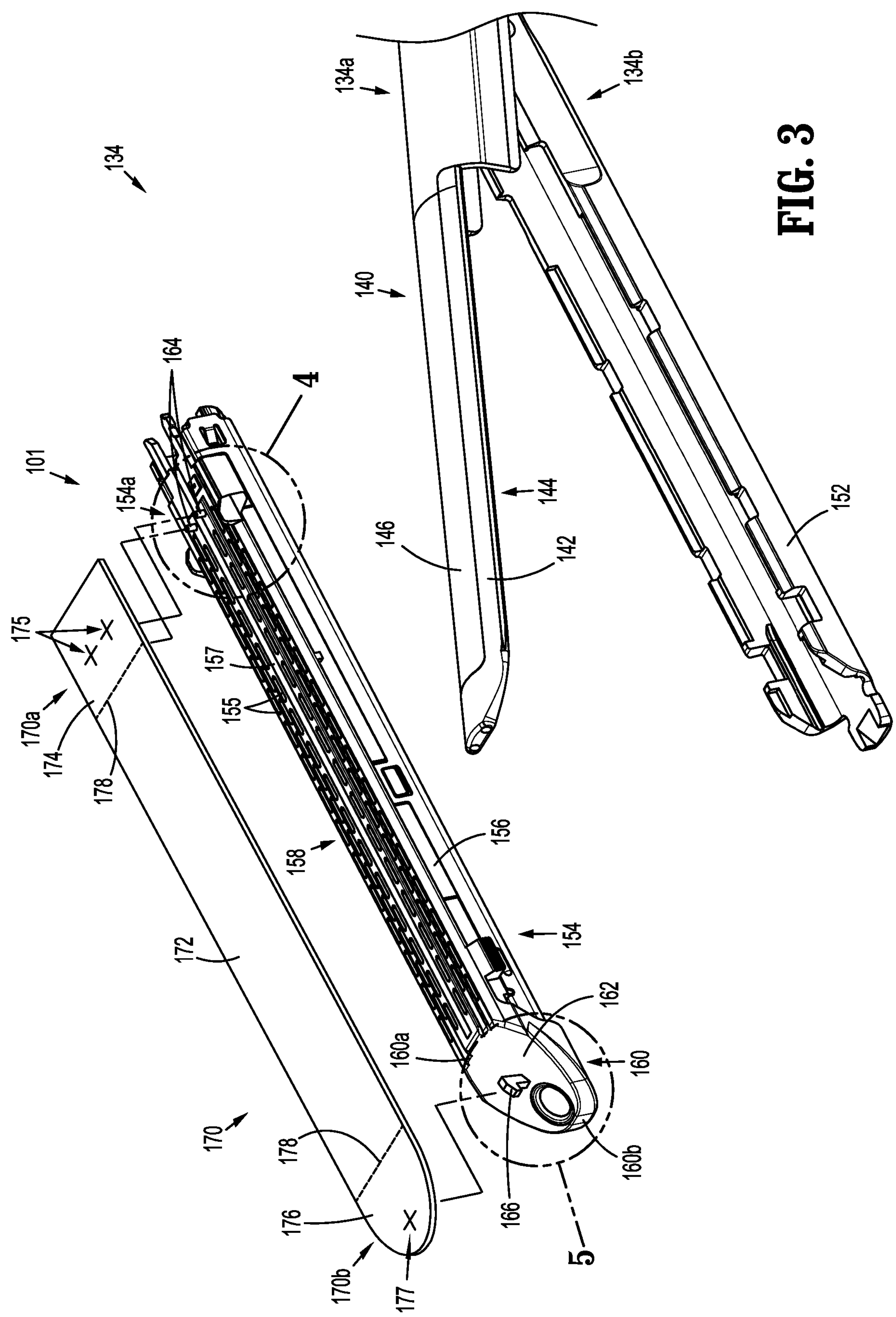
FIG. 3 is a perspective view, with parts separated, of the tool assembly of FIG. 2, the tool assembly including a surgical buttress attachment assembly in accordance with an aspect of the disclosure.

The loading unit 130 is a disposable loading unit ("DLU") that is releasably secured to the elongated tubular body 124 and thus, replaceable with a new loading unit 130. The loading unit 130 may be a single use loading unit ("SULU") that is used one time and then replaced to facilitate multiples uses of the surgical stapling apparatus 100 on a patient. For example, during a surgical procedure, the surgical stapling apparatus 100 can be used to staple and cut tissue, and the entire SULU is replaced after each staple and cut operation of the surgical stapling apparatus 100. The loading unit 130 may be a multi-use loading unit ("MULU") that is re-useable a predetermined number of times. For example, during a surgical procedure, the surgical stapling apparatus 100 can be used to staple and cut tissue, and a reload (e.g., a staple cartridge 154, as seen in FIG. 3) of the MULU is replaced after each staple and cut operation of the surgical stapling apparatus 100 a predetermined number of times before the entire MULU needs to be replaced. Alternatively, the loading unit 130 may be permanently affixed to the elongated tubular body 124.

The loading unit 130 includes a housing portion 132 and a tool or jaw assembly 134 including first and second jaws **134*a*, 134*b*. The first jaw 134*a* and/or the second jaw 134*b* is pivotable with respect to the housing portion 132 such that the tool assembly 134 is movable between an open position in which the first and second jaws 134*a*, 134*b* are spaced apart with respect to each other, and a closed position in which the first and second jaws 134*a*, 134*b*** are substantially adjacent each other.

Figure 2:
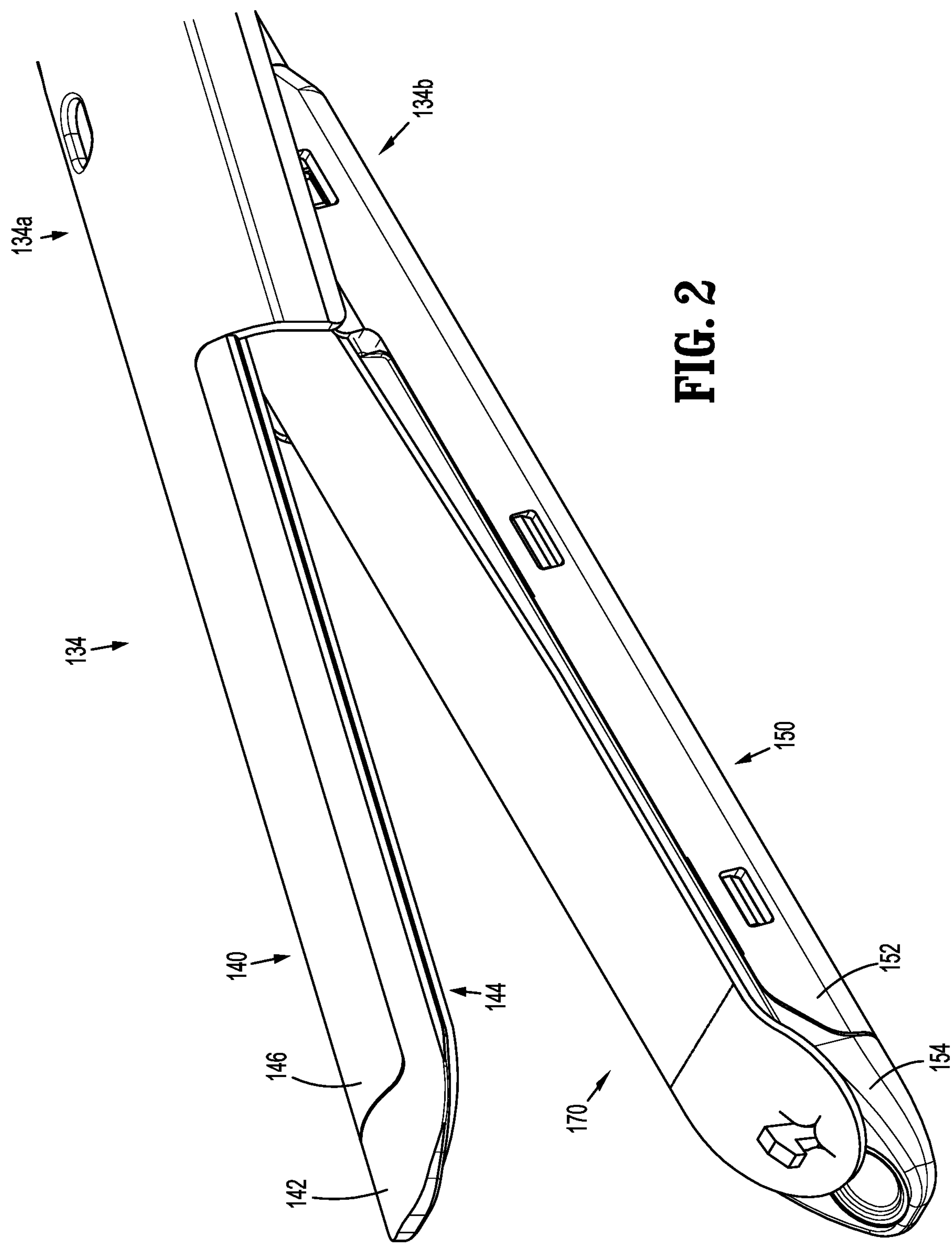
FIG. 2 is a close-up view of the area of detail 2 indicated in FIG. 1, showing a tool assembly of the surgical stapling apparatus of FIG. 1.

FIGS. 2 and 3 illustrate the first jaw **134*a* of the tool assembly 134, which includes an anvil assembly 140, and the second jaw 134*b* of the tool assembly 134, which includes a staple cartridge assembly 150 having a surgical buttress 170 releasably attached thereto. The anvil assembly 140 includes an anvil plate 142 having a tissue facing surface 144, and a cover plate 146 secured over the anvil plate 142. The staple cartridge assembly 150 includes a cartridge carrier 152 and a staple cartridge 154 selectively received and supported within the cartridge carrier 152. The staple cartridge 154 may be removably and/or replaceably attached to the cartridge carrier 152 by, for example, a snap-fit connection, a detent, a latch, among other types of connectors within the purview of those skilled in the art. Together the staple cartridge 154 and the surgical buttress 170 form a surgical buttress attachment assembly 101**.

With continued reference to FIG. 3, the staple cartridge 154 includes a cartridge body 156 having an inner or tissue facing surface 158 defining staple pockets or retention slots 155 that support staples (not shown) therein. A central longitudinal slot 157 is also defined in the tissue facing surface 158 and extends along a substantial length of the cartridge body 156 to facilitate passage of a knife (not shown) therethrough. A cartridge tip 160 extends from the cartridge body 156 distal to the staple pockets 155. The cartridge tip 160 includes an inner surface 162 contiguous with and extending distally from the tissue facing surface 158 of the cartridge body 156. The inner surface 162 may be angled or taper distally from a proximal end **160*a* of the cartridge tip 160 towards a distal end 160*a* thereof. Proximal posts 164 extend outwardly from the tissue facing surface 158 of the cartridge body 156 proximal to the staple pockets 155 and a distal post 166 extends outwardly from the inner surface 162 of the cartridge tip 160. The proximal and distal posts 164, 166 may be respectively secured to or integrally formed with the tissue facing surface 158 of the cartridge body 156 and the inner surface 162 of the cartridge tip 160. In aspects, the staple cartridge 154 is molded to include the proximal and distal posts 164, 166**.

Figure 4:
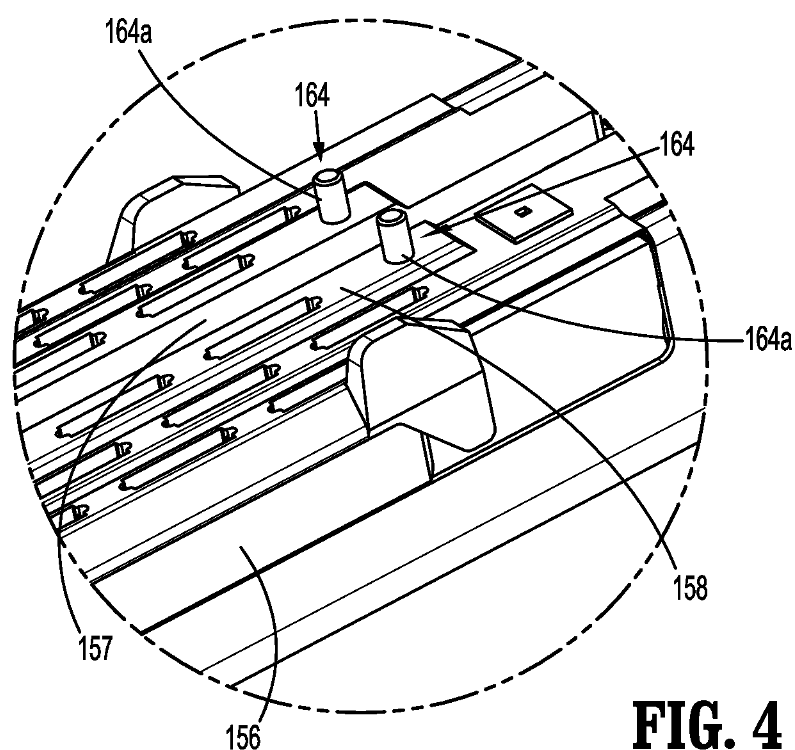
FIG. 4 is a close-up view of the area of detail 4 indicated in FIG. 3, showing a proximal end portion of a staple cartridge of the surgical buttress attachment assembly of FIG. 3.

As shown in FIGS. 3 and 4, the proximal posts 164 are disposed on opposed sides of the central longitudinal slot 157 of the cartridge body 156. Each of the proximal posts 164 is axially aligned with an innermost row of staple pockets 155, however, it should be understood that the proximal posts 164 may be otherwise laterally positioned relative to the staple pockets 155. Each of the proximal posts 164 includes an elongate body **164*a* extending outwardly from the tissue facing surface 158 of the cartridge body 156 towards the anvil assembly 140. The proximal posts 164 may be pins, poles, columns, etc. among other types of projections within the purview of those skilled in the art to which a proximal end portion 170*a* of the surgical buttress 170 may be secured. While the proximal posts 164 are shown as extending along an axis that is substantially orthogonal to an axis defined by the tissue facing surface 158 of the cartridge body 156, it should be understood that the proximal posts 164 may extend at other orientations relative to the tissue facing surface 158**, such as at a proximally extending angle.

Figure 5:
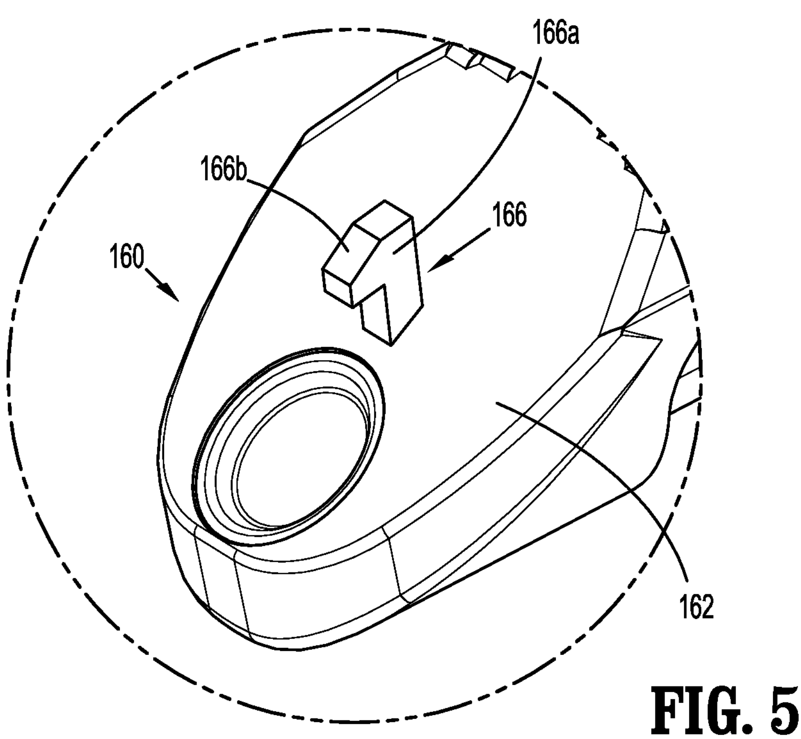
FIG. 5 is a close-up view of the area of detail 5 indicated in FIG. 3, showing a cartridge tip of the staple cartridge of the surgical buttress attachment assembly of FIG. 3.

As shown in FIGS. 3 and 5, the distal post 166 includes an elongate body **166*a* extending outwardly from the inner surface 162 of the cartridge tip 160 towards the anvil assembly 140. The distal post 166 is axially aligned with the central longitudinal slot 157 defined in the cartridge body 156. The distal post 166 further includes a flange or hook 166*b* extending distally from the elongate body 166*a* to aid in retaining a distal end portion 170*b* of the surgical buttress 170 on the staple cartridge 154. Similar to the proximal posts 164, the distal post 166 may have other configurations and/or orientations relative to the inner surface 162**.

Figure 6:
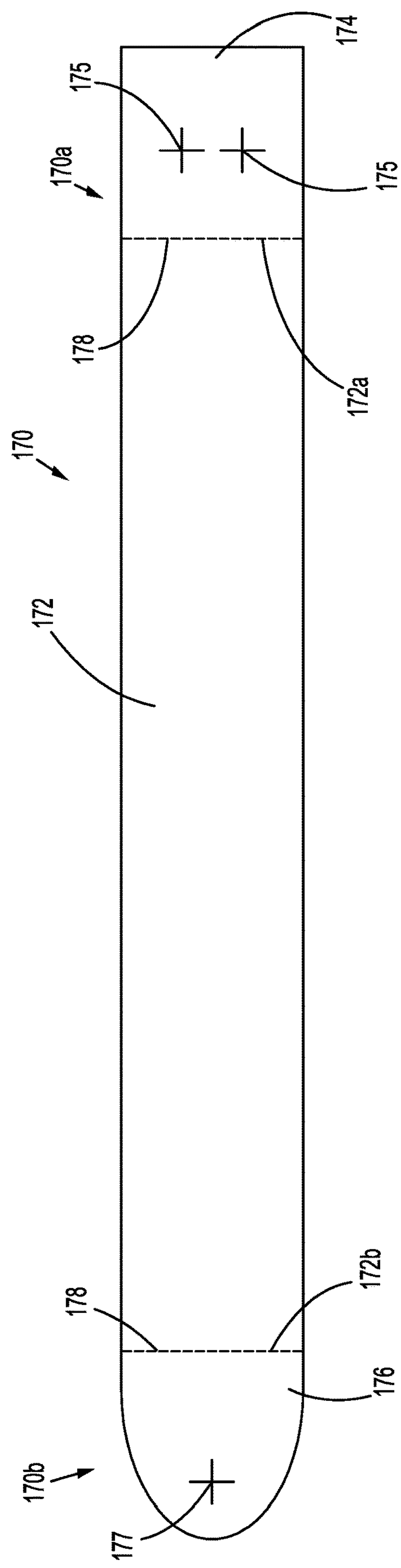
FIG. 6 is a top view of a surgical buttress of the surgical buttress attachment assembly of FIG. 3.

As shown in FIGS. 3 and 6, the surgical buttress 170 includes a body 172 having a generally rectangular shape that is configured for positioning over the staple pockets 155 of the tissue facing surface 158 of the staple cartridge 154. Proximal and distal end portions **170*a*, 170*b* of the surgical buttress 170 respectively include proximal and distal tabs 174, 176. The proximal and distal tabs 174, 176 respectively extend proximally and distally from proximal and distal ends 172*a*, 172*b* of the body 172. The proximal and distal tabs 174, 176 are delineated from the body 172 by perforations 178 extending transversely through the surgical buttress 170. The perforations 178 may be laser cut or stamped into the surgical buttress 170**.

The proximal tab 174 is sized and shaped for positioning over a proximal end portion **154*a* of the staple cartridge 154 that is proximal to the staple pockets 155 and the distal tab 176 is sized and shaped for positioning over the cartridge tip 160. While each of the proximal and distal tabs 174, 176 are shown as having a width that is substantially the same as the width of the body 172, it should be understood that the proximal and distal tabs 174, 176 may have other sizes and shapes so long as they are configured to engage the proximal and distal posts 164, 166 of the staple cartridge 154**, as described below.

The proximal tab 174 includes proximal openings 175 defined therethrough that are sized and shaped to engage the proximal posts 164 of the cartridge body 156. The distal tab 176 includes a distal opening 177 defined therethrough that is sized and shaped to engage the distal post 166 of the cartridge tip 160. The proximal and distal openings 175, 177 are pre-formed and may be slits (e.g., the "x" or "+" style slits seen in FIG. 6), holes, slots, etc. so long as the proximal and distal tabs 164, 166 can frictionally engage the respective proximal and distal posts 164, 166 via the proximal and distal openings 175, 177. Further, the proximal and distal openings 175, 177 are positioned in the respective proximal and distal tabs 174, 176 such that when the surgical buttress 170 is loaded onto the staple cartridge 154 the surgical buttress 170 is flush with the staple cartridge 154.

The surgical buttress 170 is fabricated from biocompatible materials which are bioabsorbable or non-absorbable, natural or synthetic materials. It should be understood that a single or combination of natural, synthetic, bioabsorbable, and/or non-bioabsorbable materials may be used to form the surgical buttress 170. In aspects, the surgical buttress 170 is a single sheet of material that is formed and cut to shape. In other aspects, the surgical buttress 170 is formed from a plurality of sheets of material, that are fabricated from the same or different materials, and/or the components (e.g., the body, the proximal tab, the distal tab, etc.) of the surgical buttress 170 are formed from the same or different materials that are attached to one another by, for example, welding, using adhesive, tying sutures, etc.

The surgical buttress 170 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttress 170 may be a single porous or non-porous layer, or include a plurality of layers including any combination of porous and non-porous layers. For example, the surgical buttress 170 may include multiple porous and non-porous layers that are stacked in an alternating manner. In another example, the surgical buttress 170 may be formed in a "sandwich-like" manner wherein the outer layers are porous and the inner layer(s) are non-porous, or vice versa.

Porous layer(s) in the surgical buttress 170 may enhance the ability of the surgical buttress 170 to absorb fluid, reduce bleeding, and/or seal a wound. Also, the porous layer(s) may allow for tissue ingrowth to fix the surgical buttress 170 in place. Non-porous layer(s) in the surgical buttress 170 may enhance the ability of the surgical buttress 170 to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

Figure 7:
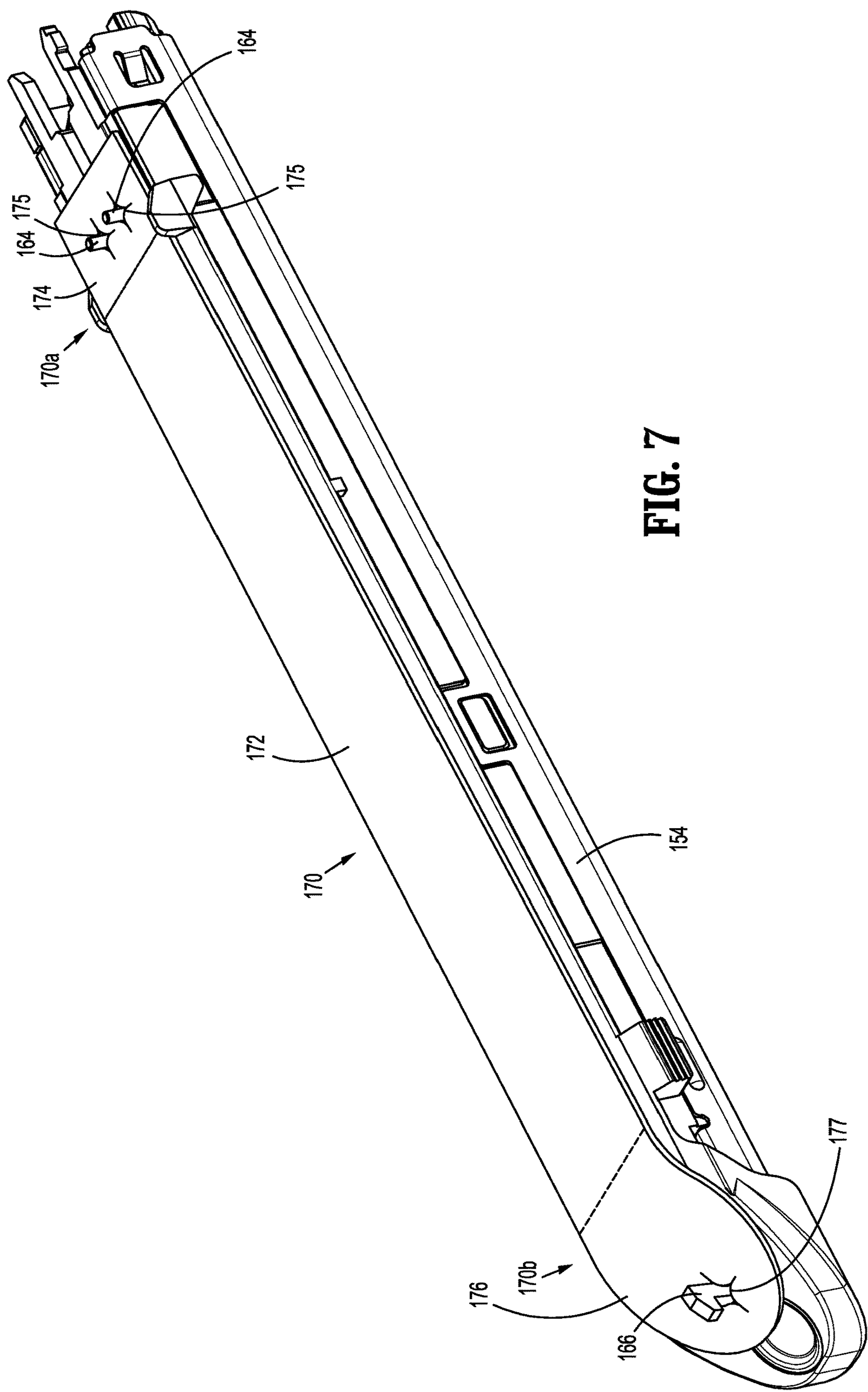
FIG. 7 is a perspective view of the surgical buttress attachment assembly of FIG. 3, showing the surgical buttress loaded on staple cartridge.

In a method of loading the surgical buttress 170 onto the staple cartridge 154, the surgical buttress 170 is positioned over the tissue facing surface 158 of the staple cartridge 154 such that the proximal openings 175 defined in the proximal tab 174 are aligned with the proximal posts 164 of the staple cartridge 154, and the distal opening 177 defined in the distal tab 176 is aligned with the distal post 166 of the staple cartridge 154, as seen in FIG. 3. The surgical buttress 170 is moved towards the staple cartridge 154 so that the proximal and distal posts 164, 166 of the staple cartridge 154 extend through the proximal and distal openings 175, 177 and engage the proximal and distal tabs 174, 176 of the surgical buttress 170 to retain the proximal and distal end portions 170*a*, 170*b* of the surgical buttress 170 on the staple cartridge 154, as seen in FIG. 7. The surgical buttress 170 is moved towards the staple cartridge 154 until the body 172 of the surgical buttress 170 lies flush against the tissue facing surface 158 (FIG. 3). The staple cartridge 154 is now loaded with the surgical buttress 170. The staple cartridge 154 may be pre-loaded with the surgical buttress 170 (e.g., by the manufacturer) or may be loaded with the surgical buttress 170 (e.g., by an end-user).

The surgical stapling apparatus 1 (FIG. 1), with the staple cartridge assembly 150 including the assembled surgical buttress attachment assembly 101, is ready for use. The surgical stapling apparatus 1 is used in accordance with methods known by those skilled in the art. Once the anvil and staple cartridge assemblies 140, 150 are clamped onto tissue, the surgical stapling apparatus 1 is fired, thereby stapling the surgical buttress 170 to the tissue. During firing, a knife (not shown) travels distally between the anvil and staple cartridge assembly 140, 150 and substantially simultaneously cuts and divides the tissue and the surgical buttress 170 disposed between the rows of formed staples. When firing is complete and the anvil and staple cartridge assemblies 140, 150 are unclamped, the body 172 of the surgical buttress 170, which is now stapled to the tissue, pulls away from the staple cartridge assembly 150, and the tool assembly 134 can be removed from the surgical site. Specifically, the body 172 of the surgical buttress 170 is freed from the staple cartridge 154 by tearing of the surgical buttress 170 away from the proximal and distal tabs 174, 176 along the perforations 178 such that the proximal and distal tabs 174, 176 remain attached to the staple cartridge 154. The used staple cartridge 154 may then be removed from the tool assembly 134 and replaced with a new staple cartridge 154. A new surgical buttress 170 may be installed onto the new staple cartridge 154, as needed or desired, as described above.

Figure 8:
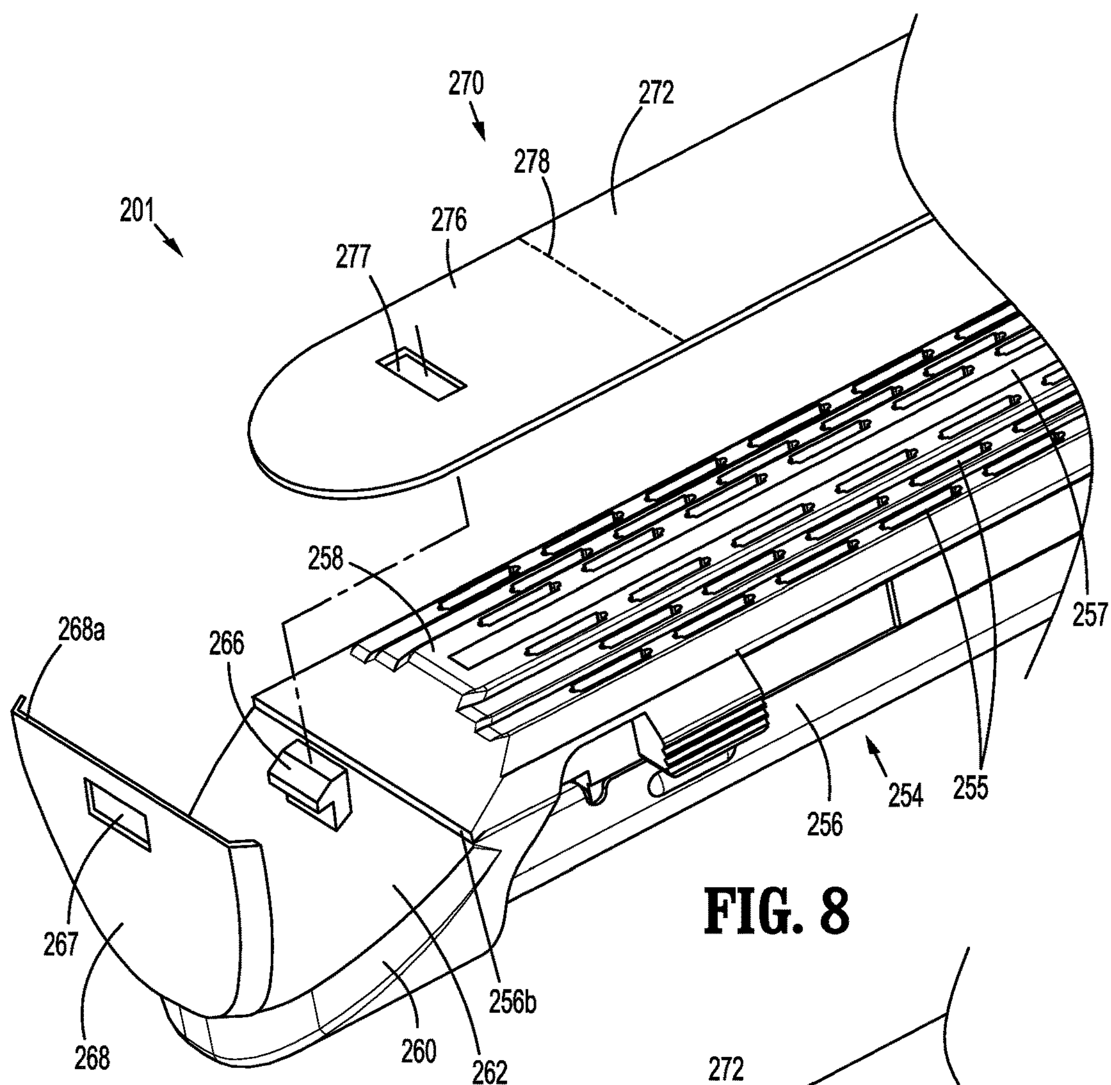
FIG. 8 is a perspective view, with parts separated, of a surgical buttress attachment assembly in accordance with another aspect of the disclosure.

Turning now to FIG. 8, a surgical buttress attachment assembly 201 in accordance with another aspect of the disclosure is shown. The surgical buttress attachment assembly 201 includes a staple cartridge 254 and a surgical buttress 270. The elements of the staple cartridge 254 and the surgical buttress 270 which are similar or identical to the staple cartridge 154 and the surgical buttress 170 of the surgical buttress attachment assembly 101 of FIG. 3 will be described briefly herein, and the differences will be described in detail herein.

The staple cartridge 254 includes a cartridge body 256 having a tissue facing surface 258 including staple pockets 255 and a central longitudinal slot 257 formed therein. The cartridge body 256 includes proximal posts (not explicitly shown) that are substantially similar or identical to the proximal posts 164 seen in FIG. 3. The staple cartridge 254 also includes a cartridge tip 260 having a distal post 266 extending outwardly from an inner surface 262 thereof. The staple cartridge 254 further includes a tip cover 268 pivotably coupled to the cartridge tip 260.

Figure 9:
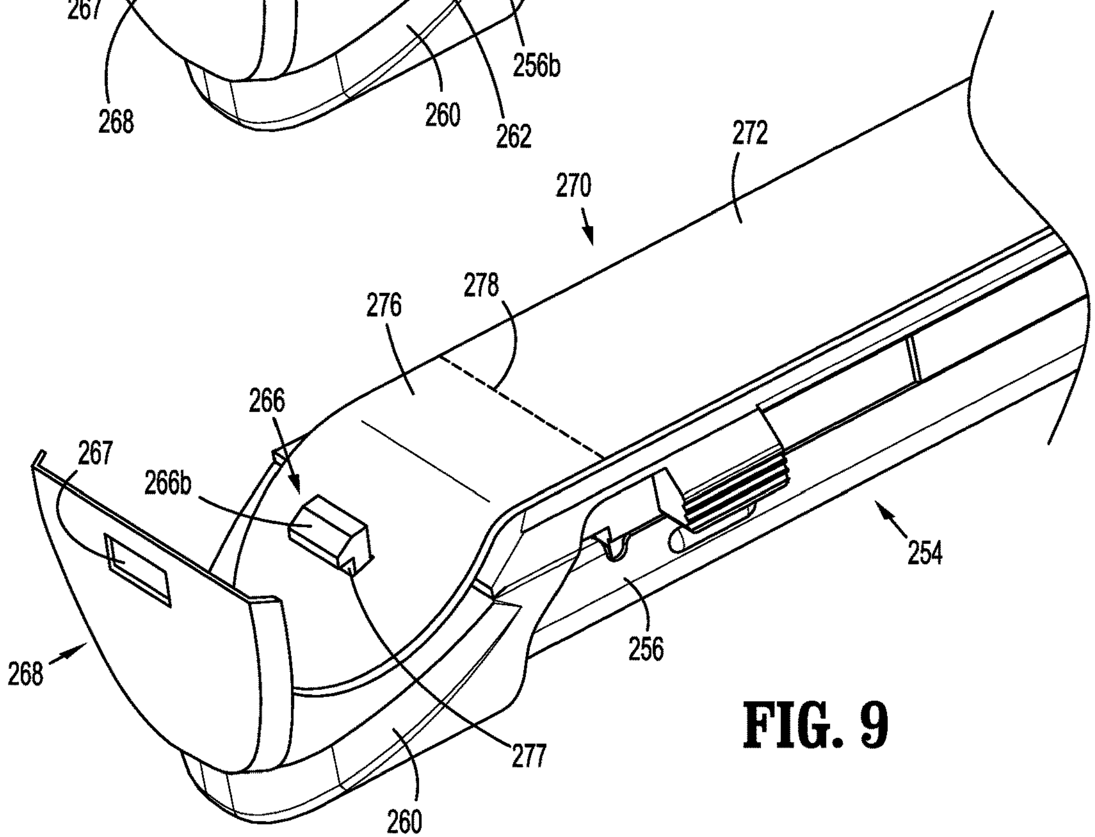
FIG. 9 is a perspective view of the surgical buttress attachment assembly of FIG. 8, showing a surgical buttress of the surgical buttress attachment assembly partially loaded on a staple cartridge of the surgical buttress attachment assembly.
Figure 10:
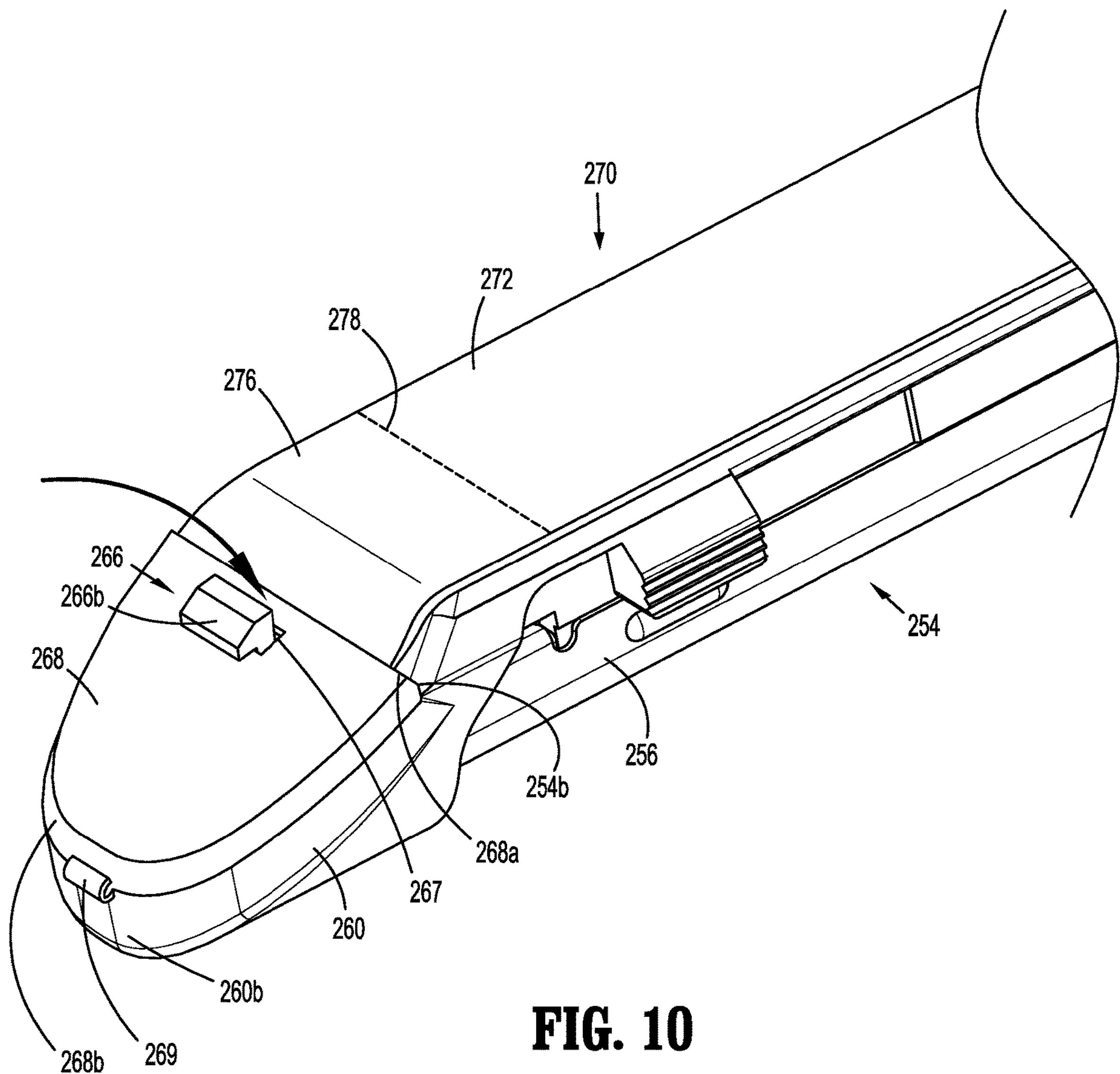
FIG. 10 is a perspective view of the surgical buttress attachment assembly of FIG. 9, shown with the surgical buttress loaded on staple cartridge.

As shown in FIGS. 8-10, a distal end 268*b* of the tip cover 268 is coupled to a distal end 260*b* of the cartridge tip 260 by a hinge 269 (FIG. 10). The tip cover 268 is movable (e.g., pivotable) relative to the cartridge tip 260 about the hinge 269 between an open position, as seen in FIGS. 8 and 9, in which the inner surface 262 of the cartridge tip 260 is uncovered, and a closed position, as seen in FIG. 10, in which the inner surface 262 of the cartridge tip 260 is covered by the tip cover 268. While the hinge 269 is shown as a living hinge, it should be understood that other hinge configurations are envisioned, such as a pivot pin extending through aligned apertures defined in the cartridge tip and the tip cover, as a ribbon cable, as a suture tether, or the like. Accordingly, the hinge 269 may be integrally formed with the cartridge tip 260 and the tip cover 268, or may be a separate component pivotably connecting the cartridge tip 260 and the tip cover 268. In aspects, the staple cartridge 254 is molded to include the cartridge tip 260, the tip cover 268, and the hinge 269. In other aspects, no hinge 269 may be used and tip cover 268 may be snap-fit or friction fit connected to distal end 260*b* of the cartridge tip 260.

The tip cover 268 is sized and shaped to extend over and engage the inner surface 262 of the cartridge tip 260, with a proximal end 268*a* of the tip cover 268 flush with a distal end 256*b* of the cartridge body 256, when the tip cover 268 is in the closed position. The tip cover 268 includes an aperture 267 defined therethrough that is sized, shaped, and positioned to receive the distal post 266 therethrough when the tip cover 268 is moved between the open and closed positions, and to engage the flange 266*b* of the distal post 266 (e.g., in a snap-fit arrangement) when in the closed position. Accordingly, deflecting the flange 266*b* of the distal post 266 proximally enables the tip cover 268 to be moved back to the open position.

The surgical buttress 270 includes a body 272, a proximal tab (not explicitly shown) that is substantially similar or identical to the proximal tab 174 seen in FIG. 3, and a distal tab 276. Perforations 278 separate the body 272 from the proximal tab (not shown, see perforations 178 in FIG. 3) and the distal tab 276. The distal tab 276 is sized and shaped for positioning over the cartridge tip 260, and between the cartridge tip 260 and the tip cover 268 when the tip cover 268 is in the closed position. The distal tab 276 includes a distal opening 277 therethrough that is sized and shaped to engage the distal post 266 of the cartridge tip 260 when the surgical buttress 270 is loaded onto the staple cartridge 254. The distal opening 277 is also positioned within the distal tab 276 such that when the surgical buttress 270 is loaded onto the staple cartridge 254 the surgical buttress 270 is flush against the staple cartridge 254.

In a method of loading the surgical buttress 270 onto the staple cartridge 254, the tip cover 268 is initially disposed in the open position, as seen in FIG. 8. The surgical buttress 270 is positioned over the tissue facing surface 258 of the staple cartridge 254 such that the distal opening 277 defined in the distal tab 276 is aligned with the distal post 266 of the staple cartridge 254. The surgical buttress 270 is moved towards the staple cartridge 254 to engage the distal tab 276 with the distal post 266, as seen in FIG. 9, via the distal opening 277. The body 272 of the surgical buttress 270 is then laid against the tissue facing surface 258 of the staple cartridge 254 and the proximal tab (not shown) is engaged with the proximal posts (not shown) in the manner described above with regard to the proximal tab 174 and the proximal posts 164 of FIGS. 3 and 7. The tip cover 268 is then pivoted to the closed position, as seen in FIG. 10, to capture and retain the distal tab 276 of the surgical buttress 270 on the staple cartridge 254. The staple cartridge 254 is now loaded with the surgical buttress 270. The surgical stapling apparatus 1 (FIG. 1), with the staple cartridge assembly 150 including the assembled surgical buttress attachment assembly 201, is used as described above with regard to the surgical buttress attachment assembly 101 of FIG. 3.

Alternatively, the distal post 266 of the staple cartridge 254 may be omitted. In such aspects, the tip cover 268 is biased in the closed position and the distal tab 276 of the surgical buttress 270 is secured to the staple cartridge 254 via the tip cover 268 after engagement of the proximal tab (not shown) with the staple cartridge 254.

Figure 11:
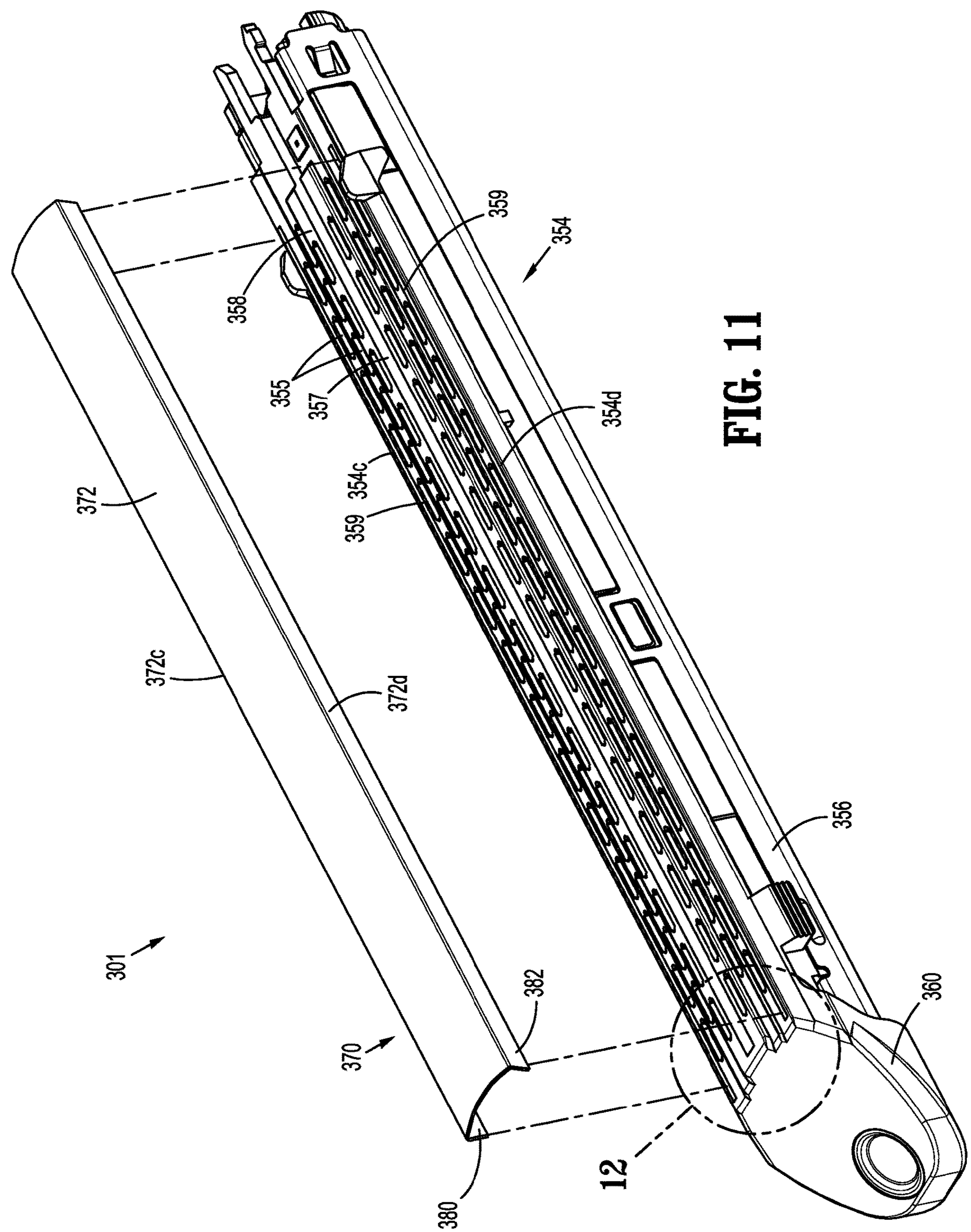
FIG. 11 is a perspective view, with parts separated, of a surgical buttress attachment assembly in accordance with yet another aspect of the disclosure.

Turning now to FIG. 11, a surgical buttress attachment assembly 301 in accordance with yet another aspect of the disclosure is shown. The surgical buttress attachment assembly 301 includes a staple cartridge 354 and a surgical buttress 370. The elements of the staple cartridge 354 and the surgical buttress 370 which are similar or identical to the staple cartridge 154, 254 and the surgical buttress 170, 270 of the surgical buttress attachment assemblies 101, 201 of FIGS. 3 and 8 will be described briefly herein, and the differences will be described in detail herein.

The staple cartridge 354 includes a cartridge body 356 and a cartridge tip 360. The cartridge body 356 has a tissue facing surface 358 including staple pockets 355 and a central longitudinal slot 357 formed therein. The staple cartridge 354 further includes longitudinal slots or channels 359 defined in the cartridge body 356.

Figure 12:
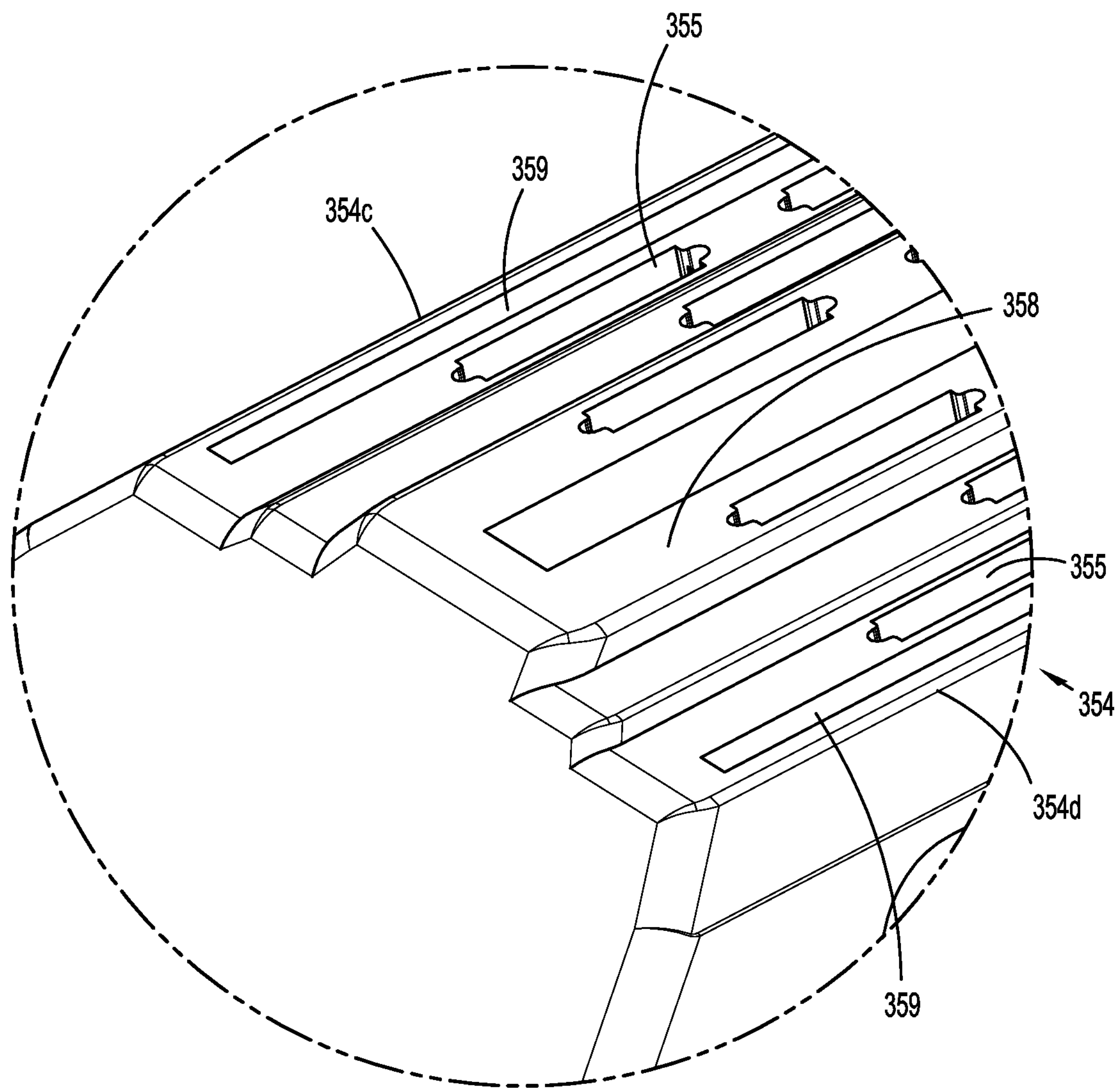
FIG. 12 is a close-up view of the area of detail 12 indicated in FIG. 11, showing a distal end portion of a staple cartridge of the surgical buttress attachment assembly of FIG. 11.

As shown in FIGS. 11 and 12, the longitudinal slots 359 are disposed on opposed sides of the tissue facing surface 358 of the staple cartridge 354 laterally outwardly of the staple pockets 355 and adjacent to longitudinal edges 354*c*, 354*d* of the staple cartridge 354. The longitudinal slots 359 continuously extend proximally and distally beyond the staple pockets 355 along a substantial length of the cartridge body 356. It is envisioned that the longitudinal slots 359 may be shorter in length (e.g., extending along a length of the staple cartridge 354 corresponding to the portion of the cartridge body 356 containing all or some the staple pockets 355) or the longitudinal slots 359 may be discontinuous and include two or more slot regions (e.g., first and second slot regions in proximal and distal portions of the cartridge body 356). In aspects, the staple cartridge 354 is molded to include the longitudinal slots 359.

As seen in FIG. 11, the surgical buttress 370 includes a body 372 and longitudinal tabs 380, 382 extending outwardly from opposed longitudinal edges 372*c*, 372*d* of the body 372. The longitudinal tabs 380, 382 extend the length of the body 372. The longitudinal tabs 380, 382 are sized and shaped for positioning within the longitudinal slots 359 of the staple cartridge 354 and are frictionally retained therein when the surgical buttress 370 is loaded onto the staple cartridge 354. It should be understood that the length of the longitudinal tabs 380, 382 corresponds with the length of the longitudinal slots 359.

Figures 13, 14:
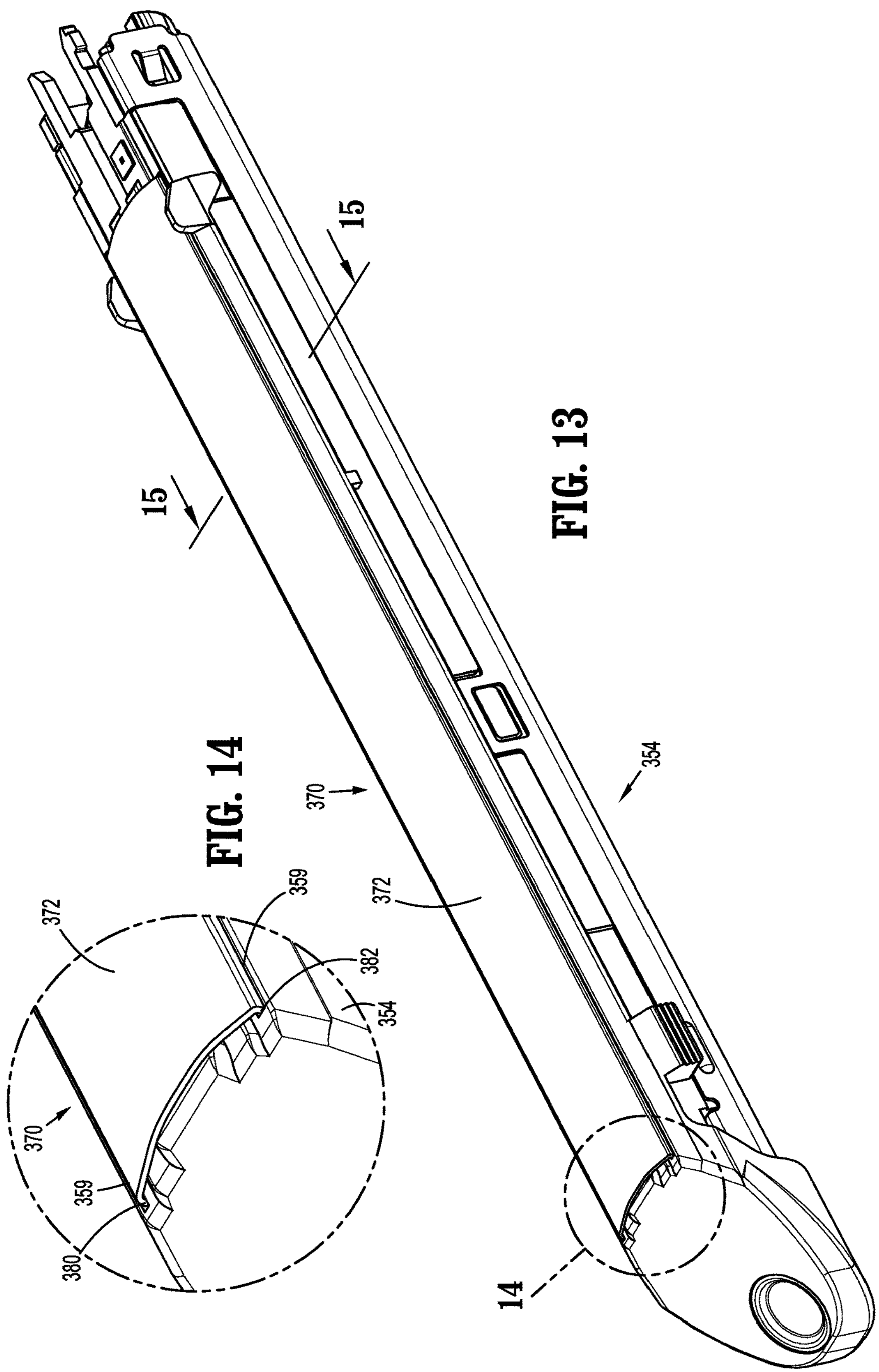
FIG. 13 is a perspective view of the surgical buttress attachment assembly of FIG. 11, showing a surgical buttress of the surgical buttress attachment assembly loaded on a staple cartridge of the surgical buttress attachment assembly.
FIG. 14 is a close-up view of the area of detail 14 indicated in FIG. 13, showing a distal end portion of the staple cartridge of the surgical buttress attachment assembly of FIG. 13.
Figure 15:
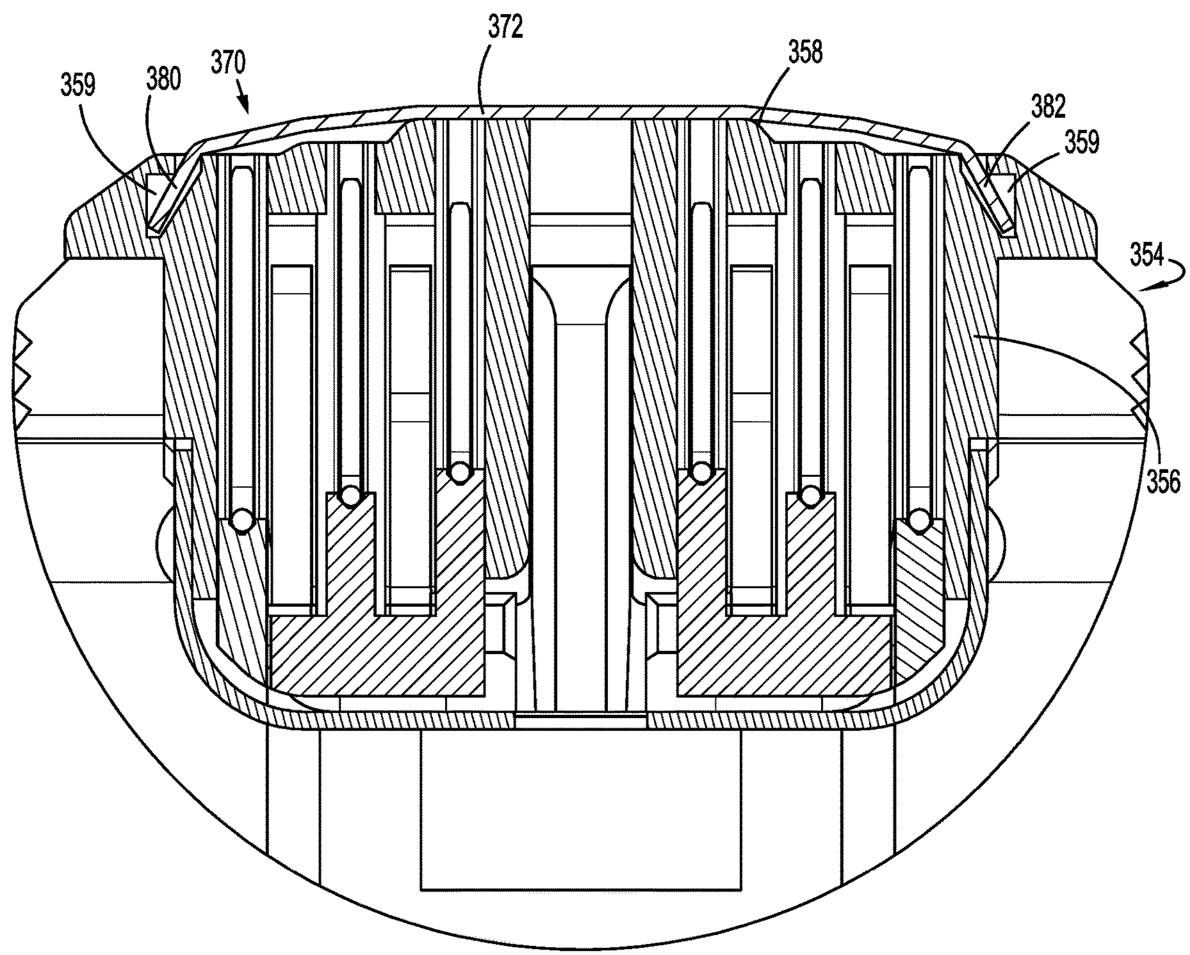
FIG. 15 is a cross-sectional view of the surgical buttress attachment assembly of FIG. 13, taken along section line 15-15 of FIG. 13.

In a method of loading the surgical buttress 370 onto the staple cartridge 354, the surgical buttress 370 is positioned over the tissue facing surface 358 of the staple cartridge 354 such that the longitudinal tabs 380, 382 are aligned with the longitudinal slots 359 of the staple cartridge 354, as seen in FIG. 11. The surgical buttress 370 is moved towards the staple cartridge 354 to feed the longitudinal tabs 380, 382 into the longitudinal slots 359 of the staple cartridge 354 until the longitudinal tabs 380, 382 are disposed within the longitudinal slots 359 and the body 372 of the surgical buttress 370 is flush against the tissue facing surface 358 of the staple cartridge 354, as seen in FIGS. 13-15. The surgical buttress 370 is retained on the staple cartridge 354 by frictional engagement of the longitudinal tabs 380, 382 with the cartridge body 356 via the longitudinal slots 359. The staple cartridge 354 is now loaded with the surgical buttress 370.

The surgical stapling apparatus 1 (FIG. 1), with the staple cartridge assembly 350 including the assembled surgical buttress attachment assembly 301, is used as described above with regard to the surgical buttress attachment assemblies 101, 201 of FIGS. 3 and 8, however, after stapling of the surgical buttress 370 to tissue, the entire surgical buttress 370 is freed from the staple cartridge 354 as the longitudinal tabs 380, 382 are pulled out of the longitudinal slots 359 when the staple cartridge assembly 150 (FIG. 1) is pulled away from the body 372 of the surgical buttress 370, which is stapled to the tissue.

It should be understood that the anvil assembly 140 (FIG. 1) may be pre-loaded and/or loaded with a surgical buttress. The surgical buttress may be retained on the anvil assembly by any suitable attachment feature within the purview of those skilled in the art, such as, for example, mechanical attachment features (e.g., a suture), chemical attachment features (e.g., adhesive), and/or attachment methods (e.g., welding). Further, while the surgical buttress retention assemblies of this disclosure are described and shown for surgical buttress attachment on the second jaw of the tool assembly, it should be understood that surgical buttress retention assemblies may additionally or alternatively be configured for use on the first jaw of the tool assembly. For example, the anvil assembly may include proximal and distal posts similar to those shown on the staple cartridge (FIG. 3), a tip cover similar to the tip cover of the staple cartridge (FIG. 8), or longitudinal slots similar to the longitudinal slots defined in the staple cartridge (FIG. 11).

While illustrated as being used on a handheld powered surgical device hereinabove, it is contemplated, and within the scope of the disclosure for the surgical buttress attachment assemblies to be configured for use with handheld manually-actuated surgical devices, as well as other electrosurgical instruments. For example, the surgical buttress assemblies may be used on handheld manually actuated surgical devices, such as those shown and described in U.S. Pat. Nos. 4,473,077, 5,915,616, 5,964,394, 6,330,965, 7,128,253, and 7,334,717, the entire contents of each of which are incorporated herein by reference. As another example, the surgical buttress attachment assemblies may be used on robotic surgical systems, such as the robotic surgical system shown and described in U.S. Pat. No. 8,828,023, the entire contents of which are incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the disclosure, and that such modifications and variation are also included within the scope of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical buttress attachment assembly for use with a surgical stapling apparatus, the surgical buttress attachment assembly comprising:

a staple cartridge including a cartridge body and a cartridge tip extending distally from the cartridge body, the cartridge body having a tissue facing surface including staple pockets defined therein and the cartridge tip including an inner surface extending distally from the tissue facing surface, the cartridge body including proximal posts extending outwardly from the tissue facing surface and the cartridge tip including a distal post extending outwardly from the inner surface, wherein the staple cartridge further includes a tip cover pivotably coupled to the cartridge tip; and a surgical buttress including a body, a proximal tab extending proximally from the body, and a distal tab extending distally from the body, the proximal tab engaged with the proximal posts of the cartridge body and the distal tab engaged with the distal post of the cartridge tip to retain the surgical buttress on the staple cartridge, wherein the distal tab of the surgical buttress is retained between the cartridge tip and the tip cover.

2. The surgical buttress attachment assembly according to claim 1, wherein the proximal posts of the cartridge body are proximal to the staple pockets.

3. The surgical buttress attachment assembly according to claim 1, wherein the tissue facing surface of the cartridge body includes a central longitudinal slot defined therein, and the proximal posts are disposed on opposed sides of the central longitudinal slot.

4. The surgical buttress attachment assembly according to claim 3, wherein the distal post of the cartridge tip is axially aligned with the central longitudinal slot of the cartridge body.

5. The surgical buttress attachment assembly according to claim 1, wherein the distal post includes an elongate body extending from the inner surface of the cartridge tip and a flange extending distally from the elongate body.

6. The surgical buttress attachment assembly according to claim 1, wherein the proximal and distal tabs of the surgical buttress respectively define proximal and distal openings, and the proximal and distal posts extend through the proximal and distal openings.

7. The surgical buttress attachment assembly according to claim 1, wherein the body of the surgical buttress is delineated from the proximal and distal tabs by perforations extending transversely through the surgical buttress.

8. The surgical buttress attachment assembly according to claim 1, wherein a distal end of the tip cover is coupled to a distal end of the cartridge tip by a hinge.

9. The surgical buttress attachment assembly according to claim 1, wherein the tip cover is movable between an open position, in which the inner surface of the cartridge tip is uncovered, and a closed position, in which the inner surface of the cartridge tip is covered.

10. The surgical buttress attachment assembly according to claim 9, wherein the tip cover defines an aperture therethrough, and the distal post of the cartridge tip extends through the aperture when the tip cover is in the closed position.

11. A surgical buttress attachment assembly for use with a surgical stapling apparatus, the surgical buttress attachment assembly comprising:

a staple cartridge including a cartridge body, a cartridge tip extending distally from the cartridge body, and a tip cover pivotably coupled to the cartridge tip, the cartridge body having a tissue facing surface including staple pockets defined therein and the cartridge tip including an inner surface extending distally from the tissue facing surface, the cartridge body including proximal posts extending outwardly from the tissue facing surface, wherein the tip cover is movable between an open position, in which the inner surface of the cartridge tip is uncovered, and a closed position, in which the inner surface of the cartridge tip is covered, and wherein the cartridge tip includes a distal post extending outwardly from the inner surface; and a surgical buttress including a body, a proximal tab extending proximally from the body, and a distal tab extending distally from the body, the proximal tab engaged with the proximal posts and the distal tab engaged between the cartridge tip and the tip cover to retain the surgical buttress on the staple cartridge.

12. The surgical buttress attachment assembly according to claim 11, wherein a distal end of the tip cover is coupled to a distal end of the cartridge tip by a hinge.

13. The surgical buttress attachment assembly according to claim 11, wherein the tip cover defines an aperture therethrough, and the distal post of the cartridge tip extends through the aperture when the tip cover is in the closed position.

14. The surgical buttress attachment assembly according to claim 13, wherein the distal post includes an elongate body extending from the inner surface of the cartridge tip and a flange extending distally from the elongate body, and the tip cover engages the flange of the distal post when the tip cover is in the closed position.

* * * * *